United States Patent
Goosens

(10) Patent No.: US 9,724,396 B2
(45) Date of Patent: *Aug. 8, 2017

(54) USE OF ANTAGONISTS OF GROWTH HORMONE OR GROWTH HORMONE RECEPTOR TO PREVENT OR TREAT STRESS-SENSITIVE PSYCHIATRIC ILLNESS

(71) Applicant: Massachusetts Institute of Technology, Cambridge, MA (US)

(72) Inventor: Ki Ann Goosens, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/211,441

(22) Filed: Mar. 14, 2014

(65) Prior Publication Data

US 2014/0274900 A1 Sep. 18, 2014

Related U.S. Application Data

(60) Provisional application No. 61/788,943, filed on Mar. 15, 2013.

(51) Int. Cl.
| | | |
|---|---|---|
| A01N 57/00 | (2006.01) | |
| A61K 31/66 | (2006.01) | |
| A61K 39/00 | (2006.01) | |
| A61K 38/27 | (2006.01) | |
| C12N 15/113 | (2010.01) | |

(52) U.S. Cl.
CPC .......... *A61K 38/27* (2013.01); *C12N 15/1136* (2013.01); *C12N 15/1138* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 4,857,637 A | 8/1989 | Hammonds et al. | |
| 4,997,815 A | 3/1991 | Perrine et al. | |
| 7,479,271 B2 | 1/2009 | Marquis et al. | |
| 7,632,809 B2 | 12/2009 | Chen | |
| 7,666,833 B2 | 2/2010 | Ghigo et al. | |
| 7,901,679 B2 | 3/2011 | Marquis et al. | |
| 8,013,015 B2 | 9/2011 | Harran et al. | |
| 8,293,709 B2 | 10/2012 | Ross et al. | |
| 2002/0187938 A1 | 12/2002 | Deghenghi | |
| 2003/0032636 A1 | 2/2003 | Cremers et al. | |
| 2004/0033948 A1 | 2/2004 | Chen | |
| 2005/0070712 A1 | 3/2005 | Kosogof et al. | |
| 2005/0148515 A1 | 7/2005 | Dong | |
| 2005/0187237 A1 | 8/2005 | Distefano et al. | |
| 2005/0191317 A1 | 9/2005 | Bachmann et al. | |
| 2005/0201938 A1 | 9/2005 | Bryant et al. | |
| 2005/0257279 A1 | 11/2005 | Qian et al. | |
| 2006/0025344 A1 | 2/2006 | Lange et al. | |
| 2006/0025566 A1 | 2/2006 | Hoveyda et al. | |
| 2006/0293370 A1 | 12/2006 | Saunders et al. | |
| 2007/0021331 A1 | 1/2007 | Fraser et al. | |
| 2007/0025991 A1 | 2/2007 | Pothoulakis et al. | |
| 2007/0037857 A1 | 2/2007 | Perrissoud et al. | |
| 2007/0191283 A1 | 8/2007 | Polvino | |
| 2007/0237775 A1 | 10/2007 | Kikly et al. | |
| 2007/0275877 A1 | 11/2007 | Baron et al. | |
| 2008/0058405 A1 | 3/2008 | Lewy | |
| 2008/0119540 A1 | 5/2008 | Thompson | |
| 2008/0242619 A1 | 10/2008 | Dong | |
| 2008/0261873 A1 | 10/2008 | Geesaman | |
| 2008/0262042 A1 | 10/2008 | Kajino et al. | |
| 2008/0300194 A1 | 12/2008 | Mann et al. | |
| 2009/0069245 A1 | 3/2009 | Bowers et al. | |
| 2009/0131478 A1 | 5/2009 | Dong et al. | |
| 2009/0143310 A1 | 6/2009 | Polvino et al. | |
| 2009/0149512 A1 | 6/2009 | Raun et al. | |
| 2009/0156483 A1 | 6/2009 | Dong et al. | |
| 2009/0156642 A1 | 6/2009 | Nishida et al. | |
| 2009/0163416 A1 | 6/2009 | Tulipano et al. | |
| 2009/0253673 A1 | 10/2009 | Ge et al. | |
| 2009/0275511 A1 | 11/2009 | Dong | |
| 2009/0275648 A1 | 11/2009 | Fraser et al. | |
| 2010/0021487 A1 | 1/2010 | Zorrilla et al. | |
| 2010/0086955 A1 | 4/2010 | Harran et al. | |
| 2010/0196330 A1 | 8/2010 | Ghigo et al. | |
| 2010/0196396 A1 | 8/2010 | Szentirmai et al. | |

(Continued)

FOREIGN PATENT DOCUMENTS

| | | |
|---|---|---|
| WO | WO 93/18761 A1 | 9/1993 |
| WO | WO 97/11178 A1 | 3/1997 |
| WO | WO 97/41878 A1 | 11/1997 |
| WO | WO 01/00676 A1 | 1/2001 |
| WO | WO 03/092725 A1 | 11/2003 |
| WO | WO 2004/021984 A2 | 3/2004 |
| WO | WO 2005/097830 A2 | 10/2005 |
| WO | WO 2005/112903 A2 | 12/2005 |
| WO | WO 2006/019577 A1 | 2/2006 |
| WO | WO 2008/004972 A2 | 1/2008 |
| WO | WO 2010/051447 A1 | 5/2010 |
| WO | WO 2010/132580 A2 | 11/2010 |
| WO | WO 2011/053821 A1 | 5/2011 |
| WO | WO 2013/119800 A1 | 8/2013 |
| WO | WO 2013/155504 A1 | 10/2013 |
| WO | WO 2014/027899 A1 | 2/2014 |

OTHER PUBLICATIONS

Anagnostaras et al., Hippocampus and contextual fear conditioning: recent controversies and advances. Hippocampus. 2001;11(1):8-17.
Bangasser et al., The hippocampus is necessary for enhancements and impairments of learning following stress. Nat Neurosci. Nov. 2007;10(11):1401-3. Epub Sep. 30, 2007.

(Continued)

*Primary Examiner* — Olga N Chernyshev
(74) *Attorney, Agent, or Firm* — Wolf, Greenfield & Sacks, P.C.

(57) ABSTRACT

The invention relates to methods for treating stress sensitive condition. For instance a subject having or at risk of having a stress-sensitive condition may be treated with a growth hormone (GH) antagonist in an effective amount to treat the stress sensitive condition. The GH antagonist may be, for instance, a growth hormone receptor (GHR) antagonist.

14 Claims, 6 Drawing Sheets

(56) References Cited

U.S. PATENT DOCUMENTS

| | | |
|---|---|---|
| 2010/0227806 A1 | 9/2010 | Giovanni |
| 2010/0254994 A1 | 10/2010 | Raso |
| 2010/0272734 A1 | 10/2010 | Berger et al. |
| 2010/0286152 A1 | 11/2010 | Bernasconi et al. |
| 2011/0021420 A1 | 1/2011 | Bloom et al. |
| 2011/0245160 A1 | 10/2011 | Van Der Lely |
| 2011/0245161 A1 | 10/2011 | Mintz |
| 2011/0257086 A1 | 10/2011 | Cole et al. |
| 2011/0269777 A1 | 11/2011 | Bachurin et al. |
| 2011/0318807 A1 | 12/2011 | Harran et al. |
| 2012/0095070 A1 | 4/2012 | Springer et al. |
| 2012/0129767 A1 | 5/2012 | Tulipano et al. |
| 2012/0232113 A1 | 9/2012 | Mann et al. |
| 2012/0237521 A1 | 9/2012 | Berger et al. |
| 2013/0123170 A1 | 5/2013 | Dong |
| 2013/0289068 A1 | 10/2013 | Polvino |
| 2013/0344091 A1 | 12/2013 | Berger et al. |
| 2014/0031393 A1 | 1/2014 | Nishida et al. |
| 2014/0088139 A1 | 3/2014 | Zollers et al. |
| 2014/0287997 A1 | 9/2014 | Goosens |
| 2014/0328848 A1 | 11/2014 | Feige et al. |
| 2015/0031615 A1 | 1/2015 | Dong |
| 2015/0297691 A1 | 10/2015 | Goosens |
| 2016/0058851 A1 | 3/2016 | Goosens |
| 2016/0106821 A1 | 4/2016 | Goosens |
| 2016/0243197 A1 | 8/2016 | Goosens |

OTHER PUBLICATIONS

Chaplin et al., Improvements in behaviour and self-esteem following growth hormone treatment in short prepubertal children. Horm Res Paediatr. 2011;75(4):291-303. doi: 10.1159/000322937. Epub Feb. 5, 2011.

De Quervain et al., Stress and glucocorticoids impair retrieval of long-term spatial memory. Nature. Aug. 20, 1998;394(6695):787-90.

Diano et al., Ghrelin controls hippocampal spine synapse density and memory performance. Nat Neurosci. Mar. 2006;9(3):381-8. Epub Feb. 19, 2006.

Donahue et al., Growth hormone is produced within the hippocampus where it responds to age, sex, and stress. Proc Natl Acad Sci U S A. Apr. 11, 2006;103(15):6031-6. Epub Mar. 30, 2006.

Donahue et al., Transcriptional profiling reveals regulated genes in the hippocampus during memory formation. Hippocampus. 2002;12(6):821-33.

Fleshner et al., The neurobiology of the stress-resistant brain. Stress. Sep. 2011;14(5):498-502. doi: 10.3109/10253890.2011.596865. Epub Jul. 26, 2011.

Goosens, Hippocampal regulation of aversive memories. Curr Opin Neurobiol. Jun. 2011;21(3):460-6. doi: 10.1016/j.conb.2011.04.003. Epub May 3, 2011.

Graham et al., Recombinant human growth hormone in abstinent androgenic-anabolic steroid use: psychological, endocrine and trophic factor effects. Curr Neurovasc Res. Feb. 2007;4(1):9-18.

Kaufer et al., Restructuring the neuronal stress response with anti-glucocorticoid gene delivery. Nat Neurosci. Sep. 2004;7(9):947-53. Epub Aug. 8, 2004.

Kojima et al., Ghrelin is a growth-hormone-releasing acylated peptide from stomach. Nature. Dec. 9, 1999;402(6762):656-60.

Lakshminarasimhan et al., Stress leads to contrasting effects on the levels of brain derived neurotrophic factor in the hippocampus and amygdala. PLoS One. 2012;7(1):e30481. doi: 10.1371/journal.pone.0030481. Epub Jan. 17, 2012.

Le Grevés et al., Growth hormone induces age-dependent alteration in the expression of hippocampal growth hormone receptor and N-methyl-D-aspartate receptor subunits gene transcripts in male rats. Proc Natl Acad Sci U S A. May 14, 2002;99(10):7119-23.

Lederbogen et al., City living and urban upbringing affect neural social stress processing in humans. Nature. Jun. 22, 2011;474(7352):498-501. doi: 10.1038/nature10190.

Magariños et al., Stress-induced atrophy of apical dendrites of hippocampal CA3c neurons: involvement of glucocorticoid secretion and excitatory amino acid receptors. Neuroscience. Nov. 1995;69(1):89-98.

Mahajan et al., Atypical depression in growth hormone deficient adults, and the beneficial effects of growth hormone treatment on depression and quality of life. Eur J Endocrinol. Sep. 2004;151(3):325-32.

Mahmoud et al., Growth hormone enhances excitatory synaptic transmission in area CA1 of rat hippocampus. J Neurophysiol. May 2006;95(5):2962-74. Epub Feb. 15, 2006.

Maric et al., Psychiatric and neuropsychological changes in growth hormone-deficient patients after traumatic brain injury in response to growth hormone therapy. J Endocrinol Invest. Dec. 2010;33(11):770-5. doi: 10.3275/7045. Epub May 17, 2010.

McEwen, Protective and damaging effects of stress mediators. N. Engl J Med. Jan. 15, 1998;338(3):171-9.

Meyer et al., A ghrelin-growth hormone axis drives stress-induced vulnerability to enhanced fear. Mol Psychiatry. Oct. 15, 2013. doi: 10.1038/mp.2013.135.

Meyer et al., Chronic ghrelin receptor activation enhances Pavlovian fear learning without increasing anxiety. Society for Neuroscience Abstract Viewer and Itinerary Planner. 2009;39.

Meyer et al., Poster B7: Ghrelin signaling modulates amygdala-dependent Learning. The Neuroscience of Emotion: From Reaction to Regulation. Jun. 4, 2009.

Molina et al., Growth hormone modulates hippocampal excitatory synaptic transmission and plasticity in old rats. Neurobiol Aging. Sep. 2012;33(9):1938-49. doi: 10.1016/j.neurobiolaging.2011.09.014. Epub Oct. 19, 2011.

Nyberg et al., Growth hormone and its receptors in the central nervous system—location and functional significance. Horm Res. 1996;45(1-2):18-22.

Pacold et al., Biologically active pituitary hormones in the rat brain amygdaloid nucleus. Science. Feb. 17, 1978;199(4330):804-6.

Ransome et al., Growth hormone signaling and hippocampal neurogenesis: insights from genetic models. Hippocampus. 2008;18(10):1034-50. doi: 10.1002/hipo.20463.

Raybuck et al., Double dissociation of amygdala and hippocampal contributions to trace and delay fear conditioning. PLoS One. Jan. 19, 2011;6(1):e15982. doi: 10.1371/journal.pone.0015982.

Sun et al., Local expression of GH and IGF-1 in the hippocampus of GH-deficient long-lived mice. Neurobiol Aging. Jun. 2005;26(6):929-37.

Treacy et al., Functional glucocorticoid inducible enhancer activity in the 5'-flanking sequences of the rat growth hormone gene. J Steroid Biochem Mol Biol. Jan. 1991;38(1):1-15.

Vander Weele et al., Restoration of hippocampal growth hormone reverses stress-induced hippocampal impairment. Front Behav Neurosci. Jun. 14, 2013;7:66. doi: 10.3389/fnbeh.2013.00066. eCollection 2013.

Varga et al., Synthesis and biological evaluation of antagonists of growth hormone-releasing hormone with high and protracted in vivo activities. Proc Natl Acad Sci U S A. Jan. 19, 1999;96(2):692-7.

Vyas et al., Chronic stress induces contrasting patterns of dendritic remodeling in hippocampal and amygdaloid neurons. J Neurosci. Aug. 1, 2002;22(15):6810-8.

Xin et al., Discovery and pharmacological evaluation of growth hormone secretagogue receptor antagonists. J Med Chem. Jul. 27, 2006;49(15):4459-69.

Makatsori et al., Modulation of neuroendocrine response and non-verbal behavior during psychosocial stress in healthy volunteers by the glutamate release-inhibiting drug lamotrigine. Neuroendocrinology. Jan. 2004;79(1):34-42.

Telegdy et al., Neurotransmitter-mediated action of an antagonist of growth hormone-releasing hormone on anxiolysis in mice. Behav Brain Res. Jul. 15, 2012;233(1):232-6. doi: 10.1016/j.bbr.2012.04.011. Epub May 5, 2012.

Krishnan et al. Animal models of depression: molecular perspectives. Curr Top Behav Neurosci. 2011;7:121-47. doi: 10.1007/7854_2010_108.

(56) References Cited

OTHER PUBLICATIONS

Pardridge, The blood-brain barrier: bottleneck in brain drug development. NeuroRx. Jan. 2005;2(1):3-14.
Rivera et al., Long-term regulated expression of growth hormone in mice after intramuscular gene transfer. Proc Natl Acad Sci U S A. Jul. 20, 1999;96(15):8657-62.
Valvassori et al., Contributions of animal models to the study of mood disorders. Rev Bras Psiquiatr. 2013;35 Suppl 2:S121-31. doi:10.1590/1516-4446-2013-1168.
Wanisch et al., Tackling obstacles for gene therapy targeting neurons: disrupting perineural nets with hyaluronidase improves transduction. PLoS One. 2013;8(1):e53269. doi: 10.1371/journal.pone.0053269. Epub Jan. 3, 2013.
Belanoff et al., Cortisol activity and cognitive changes in psychotic major depression. Am J Psychiatry. Oct. 2001;158(10):1612-6.
Birzniece et al., Growth hormone receptor modulators. Rev Endocr Metab Disord. Jun. 2009;10(2):145-56. doi: 10.1007/s11154-008-9089-x.
Chen et al., Rapid loss of dendritic spines after stress involves derangement of spine dynamics by corticotropin-releasing hormone. J Neurosci. Mar. 12, 2008;28(11):2903-11. doi: 10.1523/JNEUROSCI.0225-08.2008.
Clark et al., Long-acting growth hormones produced by conjugation with polyethylene glycol. J Biol Chem. Sep. 6, 1996;271(36):21969-77.
Cook et al., The pharmacokinetic and pharmacodynamic characteristics of a long-acting growth hormone (GH) preparation (nutropin depot) in GH-deficient adults. J Clin Endocrinol Metab. Oct. 2002;87(10):4508-14.
Fumoto et al., Targeted Gene Delivery. Importance of Administration Routes. Intech. 2013;3-31.
Jeneson et al., Working memory, long-term memory, and medial temporal lobe function. Learn Mem. Dec. 16, 2011;19(1):15-25. doi: 10.1101/1m.024018.111. Print Jan. 2012.
Jostel et al., A new sustained-release preparation of human growth hormone and its pharmacokinetic, pharmacodynamic and safety profile. Clin Endocrinol (Oxf). May 2005;62(5):623-7.
Juster et al., A transdisciplinary perspective of chronic stress in relation to psychopathology throughout life span development. Dev Psychopathol. Aug. 2011;23(3):725-76. doi: 10.1017/S0954579411000289.
Krishnan et al., Linking molecules to mood: new insight into the biology of depression. Am J Psychiatry. Nov. 2010;167(11):1305-20. doi:10.1176/appi.ajp.2009.10030434. Epub Sep. 15, 2010.
Reiter et al., A multicenter study of the efficacy and safety of sustained release GH in the treatment of naive pediatric patients with GH deficiency. J Clin Endocrinol Metab. Oct. 2001;86(10):4700-6.
Shors et al., Sex differences and opposite effects of stress on dendritic spine density in the male versus female hippocampus. J Neurosci. Aug. 15, 2001;21(16):6292-7.
Zearfoss et al., A molecular circuit composed of CPEB-1 and c-Jun controls growth hormone-mediated synaptic plasticity in the mouse hippocampus. J Neurosci. Aug. 20, 2008;28(34):8502-9. doi: 10.1523/JNEUROSCI.1756-08.2008.
Albarran-Zeckler et al., Growth hormone secretagogue receptor (GHS-R1a) knockout mice exhibit improved spatial memory and deficits in contextual memory. Behav Brain Res. Jun. 15, 2012;232(1):13-9. doi:10.1016/j.bbr.2012.03.012. Epub Mar. 31, 2012.
Alvarez-Crespo et al., The amygdala as a neurobiological target for ghrelin in rats: neuroanatomical, electrophysiological and behavioral evidence. PLoS One. 2012;7(10):e46321. doi: 10.1371/journal.pone.0046321. Epub Oct. 10, 2012.
Andero et al., Amygdala-dependent fear is regulated by Oprl1 in mice and humans with PTSD. Sci Transl Med. Jun. 5, 2013;5(188):188ra73. doi: 10.1126/scitranslmed.3005656.

Bednarek et al., Structure-function studies on the new growth hormone-releasing peptide, ghrelin: minimal sequence of ghrelin necessary for activation of growth hormone secretagogue receptor 1a. J Med Chem. Nov. 16, 2000;43(23):4370-6.
Betley et al., Neurons for hunger and thirst transmit a negative-valence teaching signal. Nature. May 14, 2015;521(7551):180-5. doi: 10.1038/nature14416. Epub Apr. 27, 2015.
Bramham et al., BDNF function in adult synaptic plasticity: the synaptic consolidation hypothesis. Prog Neurobiol. Jun. 2005;76(2):99-125.
Briggs et al., Evidence that diet-induced hyperleptinemia, but not hypothalamic gliosis, causes ghrelin resistance in NPY/AgRP neurons of male mice. Endocrinology. Jul. 2014;155(7):2411-22. doi:10.1210/en.2013-1861. Epub Apr. 17, 2014.
Brioni et al., Involvement of the amygdala GABAergic system in the modulation of memory storage. Brain Res. May 15, 1989;487(1):105-12.
Cahill et al., Amygdala activity at encoding correlated with long-term, free recall of emotional information. Proc Natl Acad Sci U S A. Jul. 23, 1996;93(15):8016-21.
Carlini et al., Differential role of the hippocampus, amygdala, and dorsal raphe nucleus in regulating feeding, memory, and anxiety-like behavioral responses to ghrelin. Biochem Biophys Res Commun. Jun. 16, 2004;313(3):635-41.
Carlini et al., Ghrelin increases anxiety-like behavior and memory retention in rats. Biochem Biophys Res Commun. Dec. 20, 2002;299(5):739-43.
Carvajal et al., Central ghrelin increases anxiety in the Open Field test and impairs retention memory in a passive avoidance task in neonatal chicks. Neurobiol Learn Mem. May 2009;91(4):402-7. doi: 10.1016/j.nlm.2008.12.008. Epub Jan. 31, 2009.
Castellano et al., Interaction of beta-endorphin and GAB Aergic drugs in the regulation of memory storage. Behav Neural Biol. Sep. 1993;60(2):123-8.
Codner et al., Effects of oral administration of ibutamoren mesylate, a nonpeptide growth hormone secretagogue, on the growth hormone-insulin-like growth factor I axis in growth hormone-deficient children. Clin Pharmacol Ther. Jul. 2001;70(1):91-8.
Conrad, A critical review of chronic stress effects on spatial learning and memory. Prog Neuropsychopharmacol Biol Psychiatry. Jun. 30, 2010;34(5):742-55. doi:10.1016/j.pnpbp.2009.11.003. Epub Nov. 10, 2009.
Cordero et al., A role for brain glucocorticoid receptors in contextual fear conditioning: dependence upon training intensity. Brain Res. Mar. 9, 1998;786(1-2):11-7.
Cowley et al., The distribution and mechanism of action of ghrelin in the CNS demonstrates a novel hypothalamic circuit regulating energy homeostasis. Neuron. Feb. 20, 2003;37(4):649-61.
Cummings et al., A preprandial rise in plasma ghrelin levels suggests a role in meal initiation in humans. Diabetes. Aug. 2001;50(8):1714-9.
Dietrich et al., Hypothalamic Agrp neurons drive stereotypic behaviors beyond feeding. Cell. Mar. 12, 2015;160(6):1222-32. doi:10.1016/j.cell.2015.02.024. Epub Mar. 5, 2015.
Dudai, The neurobiology of consolidations, or, how stable is the engram? Annu Rev Psychol. 2004;55:51-86.
Finsterwald et al., Stress and glucocorticoid receptor-dependent mechanisms in long-term memory: from adaptive responses to psychopathologies. Neurobiol Learn Mem. Jul. 2014;112:17-29. doi: 10.1016/j.nlm.2013.09.017. Epub Oct. 7, 2013.
Garin et al., Clinical review: The human experience with ghrelin administration. J Clin Endocrinol Metab. May 2013;98(5):1826-37. doi: 10.1210/jc.2012-4247. Epub Mar. 26, 2013.
Ghersi et al., Ghrelin increases memory consolidation through hippocampal mechanisms dependent on glutamate release and NR2B-subunits of the NMDA receptor. Psychopharmacology (Berl). May 2015;232(10):1843-57. doi:10.1007/s00213-014-3817-6. Epub Dec. 4, 2014.
Goldstone et al., Ghrelin mimics fasting to enhance human hedonic, orbitofrontal cortex, and hippocampal responses to food. Am J Clin Nutr. Jun. 2014;99(6):1319-30. doi: 10.3945/ajcn.113.075291. Epub Apr. 23, 2014.

(56) References Cited

OTHER PUBLICATIONS

Guan et al., Distribution of mRNA encoding the growth hormone secretagogue receptor in brain and peripheral tissues. Brain Res Mol Brain Res. Aug. 1997;48(1):23-9.

Guardiola-Lemaitre et al., Agomelatine: mechanism of action and pharmacological profile in relation to antidepressant properties. Br J Pharmacol. Aug. 2014;171(15):3604-19. doi: 10.1111/bph.12720.

Harrison et al., Exploring the Structure of Human Defensive Responses from Judgments of Threat Scenarios. PLoS One. Aug. 21, 2015;10(8):e0133682. doi: 10.1371/journal.pone.0133682. eCollection 2015.

Holbrook et al., Morphine use after combat injury in Iraq and post-traumatic stress disorder. N Engl J Med. Jan. 14, 2010;362(2):110-7. doi: 10.1056/NEJMoa0903326.

Hui et al., Memory enhancement of classical fear conditioning by post-training injections of corticosterone in rats. Neurobiol Learn Mem. Jan. 2004;81(1):67-74.

Jacks et al., MK-0677, a potent, novel, orally active growth hormone (GH) secretagogue: GH, insulin-like growth factor I, and other hormonal responses in beagles. Endocrinology. Dec. 1996;137(12):5284-9.

Jasnow et al., Thy1-expressing neurons in the basolateral amygdala may mediate fear inhibition. J Neurosci. Jun. 19, 2013;33(25):10396-404. doi:10.1523/JNEUROSCI.5539-12.2013.

Kumar et al., Differential effects of chronic social stress and fluoxetine on meal patterns in mice. Appetite. May 2013;64:81-8. doi:10.1016/j.appet.2012.12.023. Epub Jan. 11, 2013.

Lee et al., Sampling blood from the lateral tail vein of the rat. J Vis Exp. May 18, 2015;(99):e52766. doi: 10.3791/52766.

Lockie et al., Diet-induced obesity causes ghrelin resistance in reward processing tasks. Psychoneuroendocrinology. Dec. 2015;62:114-20. doi: 10.1016/j.psyneuen.2015.08.004. Epub Aug. 11, 2015.

Lutter et al., The orexigenic hormone ghrelin defends against depressive symptoms of chronic stress. Nat Neurosci. Jul. 2008;11(7):752-3. doi: 10.1038/nn.2139. Epub Jun. 15, 2008.

Marin et al., Metyrapone administration reduces the strength of an emotional memory trace in a long-lasting manner. J Clin Endocrinol Metab. Aug. 2011;96(8):E1221-7. doi: 10.1210/jc.2011-0226. Epub May 18, 2011.

McIntyre et al., Amygdala norepinephrine levels after training predict inhibitory avoidance retention performance in rats. Eur J Neurosci. Oct. 2002;16(7):1223-6.

Miller et al., If it goes up, must it come down? Chronic stress and the hypothalamic-pituitary-adrenocortical axis in humans. Psychol Bull. Jan. 2007;133(1):25-45.

Nass et al., Effects of an oral ghrelin mimetic on body composition and clinical outcomes in healthy older adults: a randomized trial. Ann Intern Med. Nov. 4, 2008;149(9):601-11.

Natalucci et al., Spontaneous 24-h ghrelin secretion pattern in fasting subjects: maintenance of a meal-related pattern. Eur J Endocrinol. Jun. 2005;152(6):845-50.

Parsons et al., Implications of memory modulation for post-traumatic stress and fear disorders. Nat Neurosci. Feb. 2013;16(2):146-53. doi:10.1038/nn.3296. Epub Jan. 28, 2013.

Ribeiro et al., Ghrelin triggers the synaptic incorporation of AMPA receptors in the hippocampus. Proc Natl Acad Sci U S A. Jan. 7, 2014;111(1):E149-58. doi:10.1073/pnas.1313798111. Epub Dec. 23, 2013.

Sivertsen et al., Functionally biased signaling properties of 7TM receptors—opportunities for drug development for the ghrelin receptor. Br J Pharmacol. Dec. 2013;170(7):1349-62. doi: 10.1111/bph.12361.

Song et al., Ghrelin modulates lateral amygdala neuronal firing and blocks acquisition for conditioned taste aversion. PLoS One. Jun. 7, 2013;8(6):e65422. doi:10.1371/journal.pone.0065422. Print 2013.

Spencer et al., Ghrelin regulates the hypothalamic-pituitary-adrenal axis and restricts anxiety after acute stress. Biol Psychiatry. Sep. 15, 2012;72(6):457-65. doi: 10.1016/j.biopsych.2012.03.010. Epub Apr. 21, 2012.

Spencer et al., Ghrelin's Role in the Hypothalamic-Pituitary-Adrenal Axis Stress Response: Implications for Mood Disorders. Biol Psychiatry. Jul. 1, 2015;78(1):19-27. doi:10.1016/j.biopsych.2014.10.021. Epub Oct. 31, 2014.

Tibshirani, Regression shrinkage and selection via the lasso. J R Stat Soc: Ser B (Method) 1996;58(1):267-288.

Tolle et al., Ultradian rhythmicity of ghrelin secretion in relation with GH, feeding behavior, and sleep-wake patterns in rats. Endocrinology. Apr. 2002;143(4):1353-61.

Tronson et al., Molecular mechanisms of memory reconsolidation. Nat Rev Neurosci. Apr. 2007;8(4):262-75.

Tschöp et al., Ghrelin induces adiposity in rodents. Nature. Oct. 19, 2000;407(6806):908-13.

Tsigos et al., Hypothalamic-pituitary-adrenal axis, neuroendocrine factors and stress. J Psychosom Res. Oct. 2002;53(4):865-71.

Vaiva et al., Low posttrauma GABA plasma levels as a predictive factor in the development of acute posttraumatic stress disorder. Biol Psychiatry. Feb. 1, 2004;55(3):250-4.

Wilensky et al., Functional inactivation of the amygdala before but not after auditory fear conditioning prevents memory formation. J Neurosci. Dec. 15, 1999;19(24):RC48.

Wren et al., Ghrelin enhances appetite and increases food intake in humans. J Clin Endocrinol Metab. Dec. 2001;86(12):5992.

Zarouna et al., Mood disorders: A potential link between ghrelin and leptin on human body? World J Exp Med. May 20, 2015;5(2):103-9. doi: 10.5493/wjem.v5.i2.103. eCollection May 20, 2015.

USE OF ANTAGONISTS OF GROWTH HORMONE OR GROWTH HORMONE RECEPTOR TO PREVENT OR TREAT STRESS-SENSITIVE PSYCHIATRIC ILLNESS

RELATED APPLICATIONS

This application claims priority under 35 U.S.C. §119(e) to U.S. Provisional Application Ser. No. 61/788,943, entitled "USE OF ANTAGONISTS OF GROWTH HORMONE OR GROWTH HORMONE RECEPTOR TO PREVENT OR TREAT STRESS-SENSITIVE PSYCHIATRIC ILLNESS" filed on Mar. 15, 2013, which is herein incorporated by reference in its entirety.

FEDERALLY SPONSORED RESEARCH

This invention was made with government support under Grant No. MH084966 awarded by the National Institutes of Health and under Contract No. W911NF-10-1-0059 awarded by the U.S. Army. The government has certain rights in the invention.

BACKGROUND OF INVENTION

Stress is defined by a constellation of responses that occur when the body's ability to cope with a series of demands is exceeded (1). Stress exposure can vary in duration, and it is clear that stress "load", defined by both the length of exposure as well as the number of stressors present, plays a role in determining the consequences of stress (2). Short-term stress is thought to recruit adaptive responses that promote coping and resilience. However, the mechanisms for driving adaptive change may be difficult to maintain in the face of repeated challenge, and maladaptations can occur when stress is prolonged (3). For example, high stress load is a risk factor for the development of numerous types of affective mental illness, particularly those involving fear and anxiety (4-6). Despite an abundant literature on the effects of stress in the brain, most studies have focused on the effects of acute stress. Thus, the mechanisms that lead to maladaptations following chronic stress exposure are unclear.

While there are many brain regions that are altered by stress and mediate stress-related changes in behavior, the hippocampus is the region in which the effects of stress are best characterized. The hippocampus plays a role in many types of memory (7), and is also linked to affective regulation (8, 9). Acute stress can both enhance and impair hippocampal function. For example, acute stress can increase (10) or decrease (11) hippocampal dendritic spine density. Acute stress can also enhance (12) or impair (13) hippocampus-dependent cognition, perhaps depending on the level of arousal attained during the stress (14). In contrast, chronic stress generally produces dendritic retraction in hippocampus (15-18), and impairs performance on hippocampus-dependent memory tasks (19-21). These changes are thought to be mediated, in part, by stress hormone-induced downregulation of growth factors, such as brain-derived neurotrophic factor, in neurons (22).

SUMMARY OF INVENTION

In some aspects the invention is a method for treating a stress sensitive condition, involving administering to a subject having or at risk of having a stress-sensitive condition a growth hormone (GH) antagonist in an effective amount to treat the stress sensitive condition.

The GH antagonist in some embodiments is a growth hormone receptor (GHR) antagonist, a small molecule growth hormone receptor antagonist, a protein growth hormone receptor antagonist such as pegvisomant (SOMAVERT®), B2036, B2036-PEG, G120R, G120RhGH, or analogs thereof, a GHR inverse agonist, or an inhibitory nucleic acid.

In other embodiments the stress sensitive condition is a stress sensitive disorder. The stress-sensitive disorder may be post-traumatic stress disorder (PTSD), bipolar disorder, acute stress disorder, generalized anxiety disorder, obsessive-compulsive disorder, panic disorders, schizophrenia, or trichotillomania. In some embodiments the stress sensitive condition is a condition associated with chronic stress. For instance, the chronic stress may be associated with military service or a natural disaster.

In some embodiments the subject is diagnosed as having a stress sensitive disorder that does not involve clinical depression.

The GH antagonist may be administered systemically. In some embodiments the GH antagonist is administered to the subject orally or intravenously In some embodiments the GH antagonist is administered while the subject is experiencing the stress. In other embodiments the GH antagonist is administered only during the time that the subject is experiencing the stress. In yet other embodiments the GH antagonist is administered before, during and/or after exposure of the subject to chronic stress.

According to other embodiments the GH antagonist is administered to the subject in a sustained release device.

In yet other embodiments the GH antagonist is delivered to the amygdala.

Use of a compound of the invention for treating a stress sensitive condition is also provided as an aspect of the invention.

A method for manufacturing a medicament of a compound of the invention for treating a stress sensitive condition is also provided.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The accompanying drawings are not intended to be drawn to scale. For purposes of clarity, not every component may be labeled in every drawing. In the drawings.

DETAILED DESCRIPTION

Figure 1:
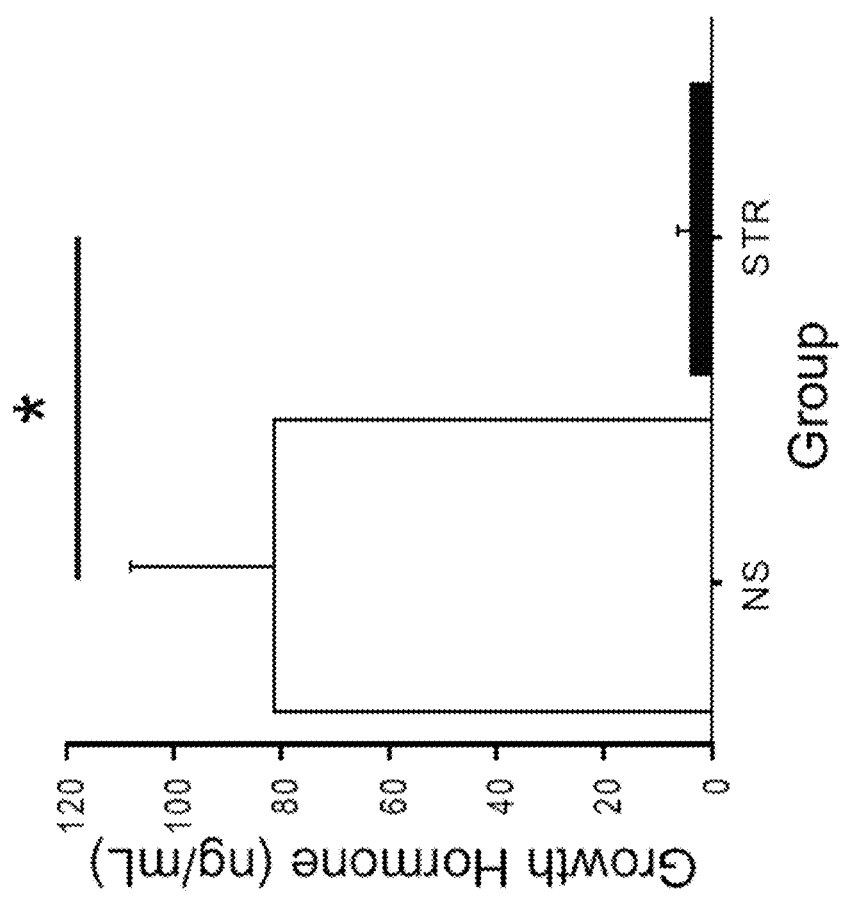
FIG. 1 shows that chronic stress reduces hippocampal growth hormone (GH). Hippocampal GH levels were assayed seven days after a two week period of immobilization stress (STR) or handling (NS). GH was significantly lower in the hippocampi of stressed rats relative to unstressed rats.

Growth hormone (GH) is a hormone released into the circulating blood stream by the pituitary, but it is also synthesized by the hippocampus and other brain regions (23, 24). Within the hippocampus, application of exogenous GH is sufficient to induce synaptic plasticity (25). Exogenous GH also facilitates hippocampal synaptic transmission (26, 27) and hippocampus-dependent eyeblink conditioning is associated with enhanced GH protein synthesis in hippocampal cells (28). Interestingly, hippocampal GH levels are stress-sensitive: GH gene transcription is regulated by glucocorticoid stress hormones, and GH protein levels are increased one day after an acute stress exposure (30). However, these studies are largely correlational. It was discovered according to the invention that higher levels of hippocampal GH may promote hippocampal function. In contrast, it was found that endogenous amygdala growth hormone levels become elevated with repeated exposure to stress.

Although growth hormone (GH) is synthesized in hippocampal neurons, where it is regulated by stress exposure, its function is poorly characterized. The invention is based at least in part on the finding that modulation of GH in different regions of the brain has an impact on stress sensitive conditions and may be used as a therapeutic intervention in the treatment of these diseases.

This invention pertains to several surprising discoveries linking exposure to growth hormone with excessive negative affect, particularly in the amygdala. In particular, the data provided in the Examples section shows that prolonged exposure of the amygdala to growth hormone (targeting brain circuits relating to negative emotion with viral vectors) potentiates negative emotional states. Endogenous amygdala growth hormone levels become elevated with repeated exposure to stress. Further, the data provided herein shows that growth hormone levels are elevated in the amygdala of human suicide completers. Growth hormone is a peripheral hormone which does not cross the blood-brain bather. Though it is made in neurons of regions such as the amygdala, virtually nothing is known about its function in those cells. Thus, a link between growth hormone and negative emotion is not intuitive, nor something that is previously described in the art.

Thus, in some aspects, the invention is a method for treating a stress sensitive condition, by administering to a subject having or at risk of having a stress-sensitive condition a growth hormone (GH) antagonist in an effective amount to treat the stress sensitive condition.

The growth hormone antagonist is useful for preventing the development of the stress sensitive condition and for treating the stress sensitive condition. As such it can be administered to the subject either prior to or during the stress exposure, or following the stress exposure.

A growth hormone antagonist, as used herein, refers to a compound that prevents, inhibits or reduces to any extent activation or expression of the growth hormone receptor. The compound that prevents or inhibits activation of the growth hormone receptor may act directly or indirectly on the growth hormone receptor. For example the compound may bind or interact directly with the growth hormone receptor in some embodiments. In other embodiments the compound may act indirectly by blocking access of the endogenous neuronal growth hormone to the growth hormone receptor. For instance the compound may be able to block access of the endogenous neuronal growth hormone to the growth hormone receptor by interfering with the expression or activity of growth hormone or blocking the growth hormone receptor binding site on growth hormone or by preventing the release of endogenous neuronal growth hormone.

The GH antagonist may be, for instance, a growth hormone receptor (GHR) antagonist. GHR antagonists include small molecule, protein and nucleic acid growth hormone receptor antagonists. Protein or peptide GHR antagonists are well known in the art and include, but are not limited to pegvisomant (SOMAVERT®), B2036, B2036-PEG, G120R, G120RhGH, or analogs thereof.

The hormone-receptor complex between hGH and the extracellular domain of its receptor (hGHbp) is known, Wells et al, Annu. Rev. Biophys. Biomol. Struct., 22:329 (1993). High-resolution structural and mutational analysis and structural analysis has shown that one molecule of hGH binds two receptor molecules sequentially using distinct sites on the hormone, called sites 1 and 2, Cunningham et al, Science, 244:1081 (1989); Cunningham et al, Science, 254: 821 (1991); De Vos et al, Science, 255:306 (1991). As such a number of additional GHR antagonists may be designed.

Pegvisomant is a protein (containing 191 amino acid residues) to which predominantly 4 to 6 PEG units are covalently bound.

A number of naturally occurring and recombinant mutants or variants of hGH are known and suitable for use herein as the growth hormone receptor antagonist. See, for example, Kostyo et al, Biochem. Biophys. Acta, 925:314 (1987); Lewis et al, J. Biol. Chem., 253:2679 (1978); Tokunaga et al, Eur. J. Biochem., 153:445 (1985); WO 91/05853; WO 92/09690; WO 92/19736; WO 92/21029; and WO 97/11178. As used herein, the term "variant" encompasses both naturally occurring and recombinant derivatives of hGH in which one or more of the amino acids of hGH are substituted or deleted, provided that the derivatives exhibit hGH activity. For example the hGH variant B2036 as disclosed in WO 97/11178 is also useful in the methods described herein.

B2036 has the following substitutions: H18D, H21N, G120K, R167N, K168A, D171S, K172R, E174S, I179T. Any amino acid can be substituted at G120 to generate an antagonist. For example the substitution may be lysine, arginine, tryptophan, tyrosine, phenylalanine, or glutamate. The K168A and the K172R substitutions are added to reduce the number of sites available for pegylation at the hormone-receptor site I binding interface. In contrast, the G120K substitution makes available an additional lysine for pegylation while providing an effective site 2 block. It is expected that B2036 could be further modified by restoring the glycine at residue 120, thereby generating a candidate for use as an antagonist that is expected to have reduced antigenicity in humans in comparison with other variants, for example 852d.

In some embodiments, the GHR antagonist is a polyethylene glycol (PEG)-modified growth hormone. As used herein, the terms "polyethylene glycol modified", "PEG-modified" and "pegylated" are used synonymously to refer to a growth hormone having one or more polyethylene glycol groups covalently bound thereto. As such the GHR antagonist may be covalently attached, or conjugated, to one or more PEG groups. Such conjugation produces a growth hormone conjugate having a greater actual molecular weight than the unmodified growth hormone. The PEG can be conjugated to the growth hormone molecule at one or more amino acid residues, including lysine residues. One or more additional water-soluble poly(alkylene oxide) polymers having a linear or branched chain may be employed in addition to PEG.

The number of lysines in growth hormone may also be modified to create additional GHR antagonists. These modifications can be made using standard mutagenesis techniques. Thus, to the extent that amino acid substitutions introduce or replace lysines, GHR antagonists of the invention can contain a greater or lesser number of potential pegylation sites than wild-type GH. The B2036 variant contains nine potential pegylation sites, one fewer than wild-type GH.

Additional GH antagonists are described in Varga et al Proc. Natl. Acad. Sci. USA Vol. 96, pp. 692-697, January 1999. For example, the following analogs were determined by Varga et al to have a high and or protracted antagonistic activity: [PhAc-Tyr1,DArg2, Phe(4-Cl)6,Arg9,Abu15, Nle27,D-Arg29]hGH-RH(1-29)$NH_2$ (JV-1-10), [PhAc-Tyr1,D-Arg2,Phe(4-Cl)6,Abu15,Nle27, D-Arg28,Har29] hGH-RH(1-29)$NH_2$ (MZ-6-55), [PhAc-Tyr1,DArg2, Phe(4-Cl)6,Arg9,Abu15,Nle27,D-Arg28,Har29]hGH-RH(1-29) $NH_2$ (JV-1-36), and [PhAc-Tyr1,D-Arg2,Phe(4-Cl)6, Har9, Tyr(Me)10,Abu15,Nle27,D-Arg28,Har29]hGH-RH(1-29) $NH_2$ (JV-1-38).

In other embodiments the GH antagonist is a GHR inverse agonist or an inhibitory nucleic acid. The GH antagonist that is an inhibitory nucleic acid may be, for instance, an siRNA or an antisense molecule that inhibits expression of a GH protein or a GHR. The nucleic acid sequences of GH and GHR are well known in the art. See for instance, Gene ID: 2688 and 2690 in NCBI database for hGH and hGHR respectively. The inhibitory nucleic acids may be designed using routine methods in the art.

A GH or GHR inhibitory nucleic acid typically causes specific gene knockdown, while avoiding off-target effects. Various strategies for gene knockdown known in the art can be used to inhibit gene expression. For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, and other small interfering nucleic acid-based molecules known in the art. In one embodiment, vector-based RNAi modalities (e.g., shRNA expression constructs) are used to reduce expression of a gene (e.g., a target nucleic acid such as a GH or GHR nucleic acid) in a cell. In some embodiments, therapeutic compositions of the invention comprise an isolated plasmid vector (e.g., any isolated plasmid vector known in the art or disclosed herein) that expresses a small interfering nucleic acid such as an shRNA. The isolated plasmid may comprise a specific promoter operably linked to a gene encoding the small interfering nucleic acid. In some cases, the isolated plasmid vector is packaged in a virus capable of infecting the individual. Exemplary viruses include adenovirus, retrovirus, lentivirus, adeno-associated virus, and others that are known in the art and disclosed herein.

A broad range of RNAi-based modalities could be employed to inhibit expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluoyl nucleotides maintain gene silencing activity (Xia et al., ASC Chem. Biol. 1(3): 176-83, (2006)). siRNAs with amide-linked oligoribonucleosides have been generated that are more resistant to S1 nuclease degradation than unmodified siRNAs (Iwase R et al. 2006 Nucleic Acids Symp Ser 50: 175-176). In addition, modification of siRNAs at the 2'-sugar position and phosphodiester linkage confers improved serum stability without loss of efficacy (Choung et al., Biochem. Biophys. Res. Commun. 342(3):919-26, 2006). Other molecules that can be used to inhibit expression of a gene (e.g., a CSC-associated gene) include sense and antisense nucleic acids (single or double stranded), ribozymes, peptides, DNA-zymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10): 2024-8, 1995; Quattrone et al., Cancer Res. 55(1):90-5, 1995; Lewin et al., Nat. Med. 4(8):967-71, 1998). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4): 307-17, 1991; Knudsen and Nielson Nucleic Acids Res. 24(3):494-500, 1996; Taylor et al., Arch. Surg. 132(11): 1177-83, 1997). Minor-groove binding polyamides can bind in a sequence-specific manner to DNA targets and hence may represent useful small molecules for suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). The diverse array of suppression strategies that can be employed includes the use of DNA and/or RNA aptamers that can be selected to target a protein of interest (e.g, GH or GHR).

Other inhibitor molecules that can be used include sense and antisense nucleic acids (single or double stranded). Antisense nucleic acids include modified or unmodified RNA, DNA, or mixed polymer nucleic acids, and primarily function by specifically binding to matching sequences resulting in modulation of peptide synthesis (Wu-Pong, November 1994, BioPharm, 20-33). Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, Crit. Rev. in Oncogenesis 7, 151-190).

As used herein, the term "antisense nucleic acid" describes a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

In some embodiments the inhibitory nucleic acid of the invention is 100% identical to the nucleic acid target. In other embodiments it is at least 99%, 95%, 90%, 85%, 80%, 75%, 70%, or 50% identical to the nucleic acid target. The term "percent identical" refers to sequence identity between two nucleotide sequences. Percent identity can be determined by comparing a position in each sequence which may be aligned for purposes of comparison. Expression as a percentage of identity refers to a function of the number of identical amino acids or nucleic acids at positions shared by the compared sequences. Various alignment algorithms and/or programs may be used, including FASTA, BLAST, or ENTREZ-FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

An inhibitory nucleic acid useful in the invention will generally be designed to have partial or complete complementarity with one or more target genes (i.e., complementarity with one or more transcripts of GH or GHR gene). The target gene may be a gene derived from the cell, an endogenous gene, a transgene, or a gene of a pathogen which is present in the cell after infection thereof. Depending on the particular target gene, the nature of the inhibitory nucleic acid and the level of expression of inhibitory nucleic acid (e.g. depending on copy number, promoter strength) the procedure may provide partial or complete loss of function for the target gene. Quantitation of gene expression in a cell may show similar amounts of inhibition at the level of accumulation of target mRNA or translation of target protein.

"Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. As an example, the efficiency of inhibition may be determined by assessing the amount of gene product in the cell: mRNA may be detected with a hybridization probe having a nucleotide sequence outside the region used for the inhibitory nucleic acid, or translated polypeptide may be detected with an antibody raised against the polypeptide sequence of that region.

Aspects of the invention relate to the effects of stress and, in particular, chronic stress. As used herein, "stress" refers to a physical, chemical or emotional factor or combination of factors that causes bodily or mental tension and that may be a factor in disease causation. It should be appreciated that any form of stress can be compatible with aspects of the invention. Exposure to stress can be chronic or acute. As used here, "chronic stress" refers to a state of prolonged tension from internal or external stressors, which may cause various physical manifestations. The effects of chronic and acute stress can be different. Several non-limiting examples of situations where a subject could be exposed to chronic stress include military service such as a combat mission, and natural disasters, such as participation in a search-and-rescue operation or rebuilding following a natural disaster. These are encompassed within the definition of stress sensitive conditions, as used herein.

Subjects who are exposed to stress can also develop stress-sensitive disorders. As used herein, a "stress-sensitive disorder" refers to any condition, disease or disorder that results, at least in part, from exposure to stress or is exacerbated, at least in part, from exposure to stress. Non-limiting examples of stress-sensitive disorders include Post-traumatic Stress Disorder (PTSD), Bipolar Disorder, Acute Stress Disorder, anxiety disorders such as Generalized Anxiety Disorder, Obsessive-Compulsive Disorder, social anxiety disorders, Panic Disorders, schizophrenia, phobias, obsessive compulsive disorders, and Trichotillomania. It should be appreciated that any stress-sensitive disorder can be compatible with aspects of the invention.

Post-Traumatic Stress Disorder (PTSD) is an anxiety neurosis caused by exposure to psychological damage by experience beyond a usual corrective ability such as traumas of wars, natural disasters, domestic violence or sexual abuse, etc. It is believed that in addition to psychological manifestations, shrinkage of the hippocampus and dysfunction of prefrontal cortex often occurs. The principal characteristic symptoms involve re-experiencing a traumatic (i.e., psychologically distressing) event, the avoidance of stimuli associated with that event, the numbing of general responsiveness, and increased arousal. The "events" concerned are outside the range of common experiences such as simple bereavement, chronic illness and marital conflict.

Phobias include specific phobias and social phobias. Specific phobia is an anxiety disorder of which the essential feature is a persistent fear of a circumscribed stimulus, which may be an object or situation, other than fear of having a panic attack or of humiliation or embarrassment in social situations (which falls under social phobia). Examples include phobias of flying, heights, animals, injections, and blood. Simple phobias may be referred to as "specific" phobias and, in the population at large. Exposure to the phobic stimulus will almost invariably lead to an immediate anxiety response. Social phobia is characterized by the persistent fear of social or performance situations in which embarrassment may occur.

Aspects of the invention relate to methods by which the effects of recurring stress can be weakened to reduce the potentiating effects of stress on stress-sensitive mental illnesses. Methods associated with the invention comprise administration of a therapeutically effective amount of a GH antagonist to a subject.

The GH antagonist can be administered to a subject before, during and/or after exposure to chronic stress. For example, the GH antagonist can be administered to a subject in anticipation of exposure to chronic stress, such as prior to participation in a military operation. As such, the GH antagonist can protect against the consequences of exposure to chronic stress. The GH antagonist can also be administered to a subject during exposure to chronic stress to protect against the consequences of exposure to chronic stress and treat symptoms associated with the effects of chronic stress. The GH antagonist t can also be administered after exposure to chronic stress to protect against the consequences of exposure to chronic stress and treat symptoms associated with the effects of chronic stress.

Further aspects of the invention relate to determining whether a subject exposed to chronic stress has an increased risk of developing a stress-sensitive disorder. For example, if elevated levels of GH in the amygdala are detected in a subject during or after exposure to chronic stress, the subject may be considered to be at increased risk of developing a stress sensitive disorder following exposure to the chronic stress.

Administering a GH antagonist to a subject who will be exposed to chronic stress may reduce the incidence of trauma-induced disorders such as post-traumatic stress disorder (PTSD). Moreover, in the past, most stress-sensitive illnesses have been treated with the same compounds that are used to treat other mental illnesses, such as selective serotonin reuptake inhibitors (SSRIs). However, these drugs do not offer any clinical benefit to a significant number of patients diagnosed with these disorders. Having drugs with a novel mechanism of action, targeting the GHR signaling pathway, may be beneficial for patients who are resistant to traditional avenues of treatment.

The methods of the invention are useful for treating a subject in need thereof. A subject in need thereof can be a subject who will be exposed to chronic stress, is currently exposed to chronic stress or has been exposed to chronic stress. For example, a subject in need thereof may be a subject involved, or who will be involved, in a military operation or combat mission. A subject in need thereof can be a subject having or at risk of a stress sensitive disorder. For example, a subject can be a patient who is diagnosed with a stress-sensitive disorder, or a subject with a strong familial history of such disorders.

In its broadest sense, the terms "treatment" or "to treat" refer to both therapeutic and prophylactic treatments. If the subject in need of treatment is experiencing a condition (i.e., has or is having a particular condition), then "treating the condition" refers to ameliorating, reducing or eliminating one or more symptoms associated with the disorder or the severity of the disease or preventing any further progression of the disease. If the subject in need of treatment is one who is at risk of having a condition, then treating the subject refers to reducing the risk of the subject having the condition or preventing the subject from developing the condition.

A subject shall mean a human or vertebrate animal or mammal including but not limited to a dog, cat, horse, cow, pig, sheep, goat, turkey, chicken, and primate, e.g., monkey.

Therapeutic compounds associated with the invention may be directly administered to the subject or may be administered in conjunction with a delivery device or vehicle. Delivery vehicles or delivery devices for delivering therapeutic compounds to surfaces have been described. The therapeutic compounds of the invention may be administered alone (e.g., in saline or buffer) or using any delivery vehicles known in the art.

The term effective amount of a therapeutic compound of the invention refers to the amount necessary or sufficient to realize a desired biologic effect. For example, an effective amount of a therapeutic compound associated with the invention may be that amount sufficient to ameliorate one or more symptoms of a stress sensitive disorder in a subject who has been exposed to chronic stress. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic compounds being administered the size of the subject, or the severity of the disease or condition. One of ordinary skill in the art can empirically determine the effective amount of a particular therapeutic compound associated with the invention without necessitating undue experimentation.

Subject doses of the compounds described herein for delivery typically range from about 0.1 µg to 10 mg per administration, which depending on the application could be given daily, weekly, or monthly and any other amount of time there between. The doses for these purposes may range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

In some embodiments a compound of the invention is administered at a dosage of between about 1 and 10 mg/kg of body weight of the mammal. In other embodiments a compound of the invention is administered at a dosage of between about 0.001 and 1 mg/kg of body weight of the mammal. In yet other embodiments a compound of the invention is administered at a dosage of between about 10-100 ng/kg, 100-500 ng/kg, 500 ng/kg-1 mg/kg, or 1-5 mg/kg of body weight of the mammal, or any individual dosage therein.

The formulations of the invention are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of the therapeutic compound associated with the invention can be administered to a subject by any mode that delivers the therapeutic agent or compound to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, rectal and intracerebroventricular.

For oral administration, the therapeutic compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189). Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is preferred. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the to form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the therapeutic agent may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the therapeutic agent either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the therapeutic compounds of the invention. The therapeutic agent is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13 (suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of therapeutic agent. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified therapeutic agent may also be prepared in different formulations depending on the type of chemical modification or the type of device employed.

Formulations suitable for use with a nebulizer, either jet or ultrasonic, will typically comprise therapeutic agent dissolved in water at a concentration of about 0.1 to 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin Oleic acid may also be useful as a surfactant.

Formulations for dispensing from a powder inhaler device will comprise a finely divided dry powder containing therapeutic agent and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Intra-nasal delivery of a pharmaceutical composition of the present invention is also contemplated. Intra-nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The agents, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The therapeutic compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a therapeutic compound of the invention optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agents may be delivered to the brain using a formulation capable of delivering a therapeutic agent across the blood brain barrier. One obstacle to delivering therapeutics to the brain is the physiology and structure of the brain. The blood-brain barrier is made up of specialized capillaries lined with a single layer of endothelial cells. The region between cells are sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipophilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. Others are known to those of skill in the art.

The therapeutic agents of the invention may be delivered with other therapeutics for treating stress sensitive disorders.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

It is not known how GH is affected by chronic stress. To address this, GH levels in the dorsal hippocampus of rats were examined after either 14 consecutive days of immobilization stress (STR) or daily handling (no stress, or NS). Hippocampal GH was dramatically downregulated following chronic stress (FIG. 1; group: $F(1,6)=8.29$, $p<0.05$). This shows that acute and chronic stress can produce very different effects on the brain.

Figure 2:
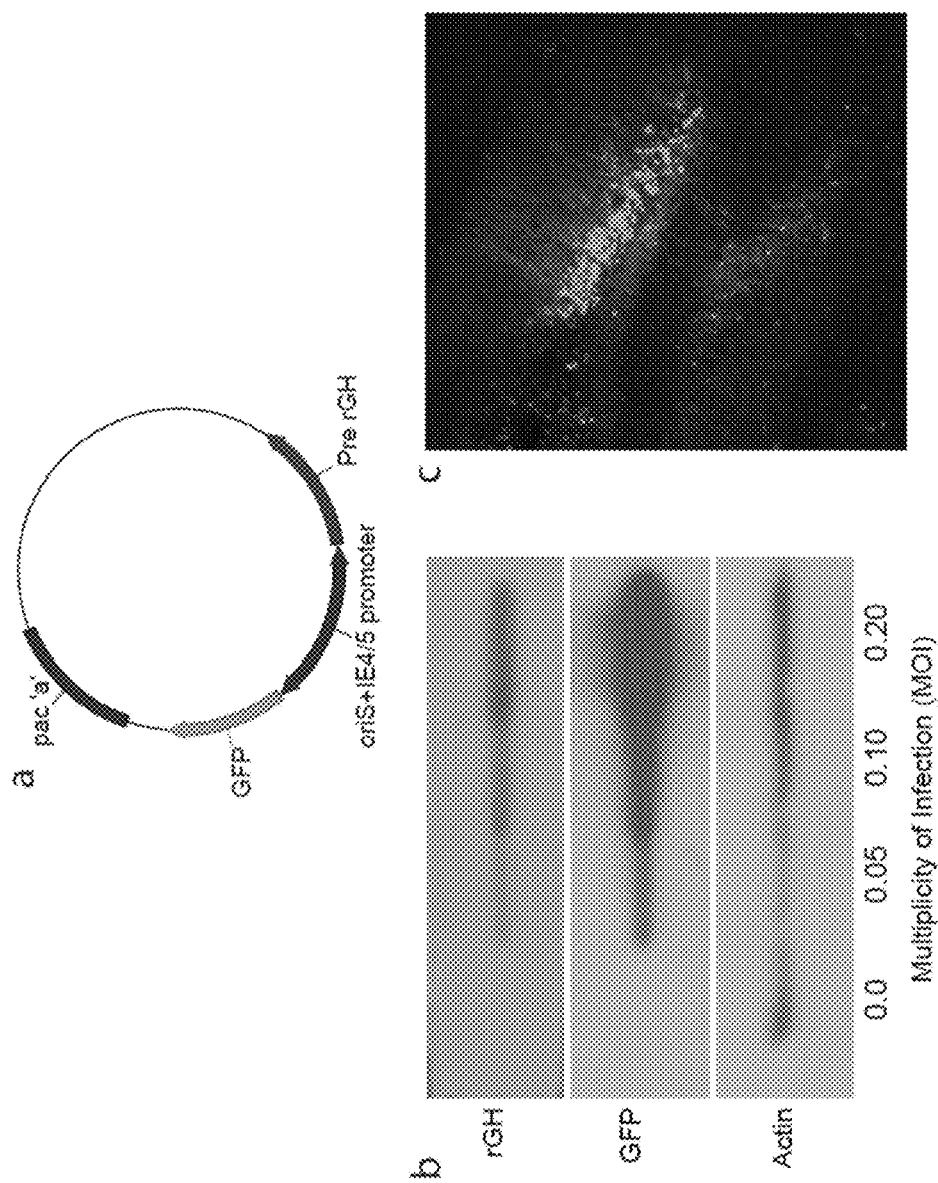
FIG. 2 shows the construction of an HSV-1 viral vector to overexpress GH. a) The full-length gene for presomatotropin was cloned into an HSV-1 amplicon under the control of the HSV α-4 promoter. eGFP was co-expressed via the HSV α-22 promoter. b) GH protein expression was confirmed in vitro. Vero cells were infected with GH virus at increasing MOIs. As the MOI increased, progressively higher levels of both GH and eGFP were detected. c) The viral vector was infused into the dorsal hippocampus of rats. A representative infection, showing high levels of expression in pyramidal cells of CA1, is shown.

Example 1: Examining the Association Between Loss of Growth Hormone in the Hippocampus and Stress-Related Changes in Hippocampal Function In order to determine whether the loss of GH in the hippocampus was associated with stress-related changes in hippocampal function, an HSV-1 based amplicon was first constructed, in which the full-length gene for rat presomatotropin (rGH), the precursor molecule for GH (31), was co-expressed with green florescent protein (GFP) under the control of a viral promoter (FIG. 2A). This amplicon, as well as a control amplicon expressing only GFP, was packaged into replication-defective HSV viral vectors. These vectors were then used to infect dorsal hippocampus (FIG. 2C). A representative infection, showing high levels of expression in pyramidal cells of CAL is shown.

Methods:

Amplicon Construction:

The rat presomatotropin gene was cloned as an 818 bp HindIII cut fragment from the p-RGH1 plasmid (31), provided by Dr. Douglas Weigent (University of Alabama at Birmingham), into the HindIII cloning site of the HSV amplicon plasmid pα22GFP (32), in which a bicistronic HSV-based promoter simultaneously drives expression of a transgene from the α-4 promoter and enhanced green florescent protein (eGFP) from the α-22 promoter. The pα22GFP plasmid was used as a control.

Virus Preparation

Virus was generated using standard methods (33). Briefly, plasmids were amplified to generate endotoxin-free DNA, which was transfected into 2-2 cells. The next day, cells were superinfected with 5dl1.2 helper virus. After two days, the cells were sonicated and centrifuged to release infectious viral particles. The resulting supernatant was twice passaged onto 2-2 cells. After the final sonication and centrifugation, the supernatant was purified on a sucrose gradient, pelleted, and resuspended in 10% sucrose in D-PBS. Aliquots of each amplicon were stored at −80° C. till use. Amplicon titers were ~1×10$^8$ IU/ml.

Subjects:

All experiments used adult male Long-Evans rats (225-275 g, Taconic, Germantown, N.Y.), housed individually (68-72° F.; 12-h light-dark cycle, 7 AM lights on). Rodent chow and water was provided ad libitum. Stressed and unstressed animals were housed in separate cubicles. All procedures were in accordance with the US National Institutes of Health (NIH) Guide for the Care and Use of Laboratory Animals and were approved by the MIT Institutional Animal Care and Use Committee, and the Animal Care and Use Review Office of the Army Research Office.

Stereotactic Virus Delivery:

Surgery was performed 18-24 h following the final handling or immobilization stress session. Rats were anesthetized (with either Nembutal at 65 mg/kg, or a ketamine:xylazine:acepromazine cocktail at 100:100:10 mg/kg, i.p.) and mounted in a stereotaxic frame. Small holes were drilled for intra-cranial placement of the injector aimed within the dorsal hippocampus: A/P −3.3, M/L+/−2.0, D/V −3.2, relative to brain surface and bregma (34). Virus was infused with either pulled glass pipettes or 33 g stainless steel bevel needles attached to a 10 ul Hamilton syringe (Hamilton Company, Reno, Nev.). The pipettes or syringes were mounted in stereotaxic barrel holder, and the rate of virus delivery was controlled by a syringe pump (Harvard Apparatus, Holliston, Mass.). Virus was infused at 0.1 ul/m for 20 m (2 ul total volume per hemisphere). Injectors remained in the brain for 10 m before being withdrawn. Incisions were closed with wound clips and Ketoprofen (1 mg, s.c.) was administered for pain and inflammation.

Protein (Western) Immunoblot:

Vero cells were plated in 6 cm dishes using standard methods (33). Purified virus was used to infect cells at multiplicities of infection ranging from 0 to 0.2. After three days, cells were harvested and homogenized. Protein was loaded on to gels for electrophoretic transfer. Membranes were incubated, in succession, with the following primary antibodies overnight at 4° C.: 1:5000 rabbit anti-GH (National Hormone and Peptide Program, NIDDK), 1:500 mouse anti-GFP (Roche, Indianapolis, Ind.), 1:1000 mouse anti-Actin (Millipore; Billerica, Mass.). Following incubation in secondary antibody, immunoreactivity was visualized using chemiluminescent detection.

Growth Hormone ELISA:

Hippocampi were homogenized 1:6 in homogenization buffer (2% HALT protease cocktail and 0.15% NP-40 in PBS) using a LabGEN 125 homogenizer (Cole-Parmer; Vernon Hills, Ill.) for 8-10 s on ice. After 5 m of incubation on ice, tubes were spun at 18,000 g for 20 m at 4° C. and the supernatant was transferred to a new tube. The resulting solution was assayed as per manufacturer's protocol (Millipore; Billerica, Mass.).

Results:

Using an antibody against rGH, confirmed that GH was expressed by cultured cells infected with the GH viral vector (FIG. 2B).

Example 2: The Role of GH in Chronic Stress-Related Changes in Auditory Trace Fear Conditioning The role of GH in chronic stress-related changes was first examined in auditory trace fear conditioning, a hippocampus-dependent task (36). Rats were repeatedly exposed to daily immobilization stress (STR) or handling (NS). One day later, rats received intra-hippocampal infusions of either GH or GFP virus. After three days for recovery, rats were subjected to auditory trace fear conditioning. Over the following two days, long-term contextual fear memory and auditory trace fear memory were assessed.

Methods:

Subjects:

Rats were treated as described in Example 2.

Experimental Methods:

Growth hormone ELISA, Protein (Western) Immunoblot methods are as described in Example 2.

Immobilization Stress:

Immobilization stress was administered for 4 h per day for 10 (contextual fear conditioning experiment) or 14 (trace fear conditioning experiment) consecutive days Animals were placed in Decapicone plastic bags (Braintree Scientific; Braintree, Mass.), which were secured at the tail to keep the bagged animal in an upright position. Stress occurred in an isolated lab room, separate from all behavioral testing space. All stress sessions were performed between 10 AM and 4 PM. Unstressed control rats were handled daily for 30 s.

Pavlovian Fear Conditioning:

All behavioral testing commenced 72 h after stereotactic viral delivery, a time point corresponding to maximal transgene expression with HSV-based viral vectors (33). Fear conditioning experiments were conducted in a modified chamber (MED Associates; St. Albans, Vt.) housed in a sound-attenuating cubicle. For auditory trace fear conditioning, rats were placed in individual chambers in a novel context (house and room lights on, 1% acetic acid, grid floors) for five minutes before receiving tone (20 s, 2 kHz, 85 dB)-footshock (1 s, 0.85 mA) pairings, with the stimuli separated by a 35 s trace interval. A 3 m inter-trial interval was used. Long-term contextual fear memory was assessed twenty-four hours later, when the rats were returned to the chambers for a 5 m context extinction test. Long-term auditory fear memory was measured twenty-four hours later; the rats were placed in the chamber configured as a novel context (room and house lights off, 0.3% Pine Sol odor, white Plexiglas floor and wall inserts). Animals were allowed 3 m to habituate to the chamber before four tones (85 dB, 2 kHz) were presented with inter-trial intervals of 3 m 35 s. For contextual fear conditioning, animals were placed in a novel context (house and room lights on, 1% acetic acid, grid floors) for three minutes before receiving three unsignaled footshocks (2 s, 0.5 mA) separated by a 90 s inter-stimulus interval. Long-term contextual memory was measured 24 h later, when the rats were returned to the context for an 8 m context test. Infrared video was recorded throughout all sessions. Freezing was measured offline using commercial software (VideoFreeze, MedAssociates, St. Albans, to VT).

Histology:

Following completion of the experiment, animals were anesthetized with an overdose of isoflurane and the brains were removed from the cranium. Brains were bisected along the midline. The dorsal hippocampus was dissected from one hemisphere, placed in a sterile eppendorf tube, and flash frozen in dimethylbutane on dry ice. The tissue was stored at $-80°$ C. The other hemisphere was placed in 4% paraformaldehyde for 72 h then transferred to a 30% sucrose/4% paraformaldehyde solution for a minimum of 3 days. Fixed tissue was cut into coronal sections on a cryostat (40 μm) and mounted on slides. Sections were assessed for GFP florescence. Animals with incorrect placements were excluded from all analyses.

Figure 3:
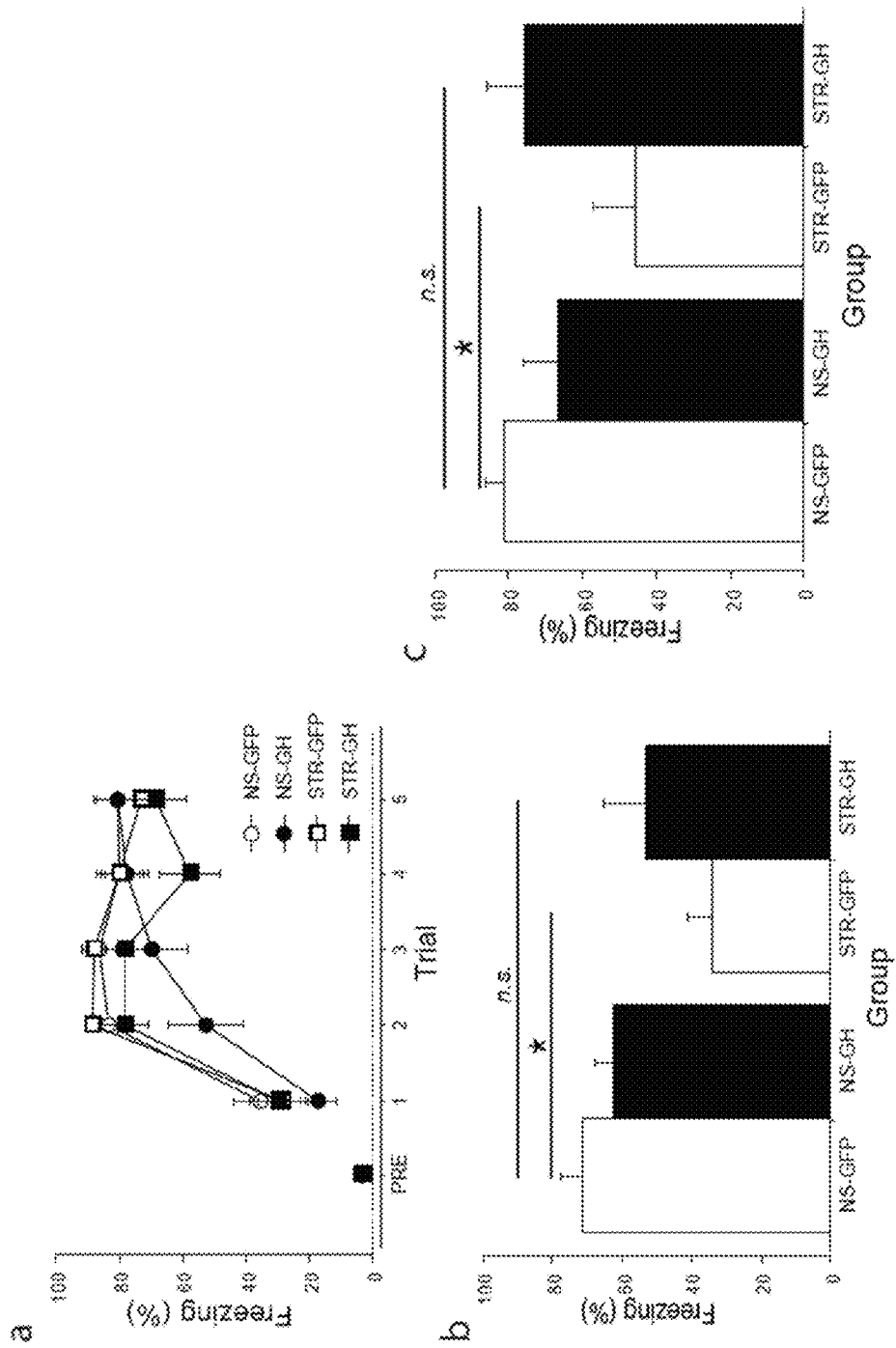
FIG. 3 shows overexpression of hippocampal GH rescues stress-related impairments in auditory trace conditioning. Two weeks of daily immobilization stress (STR) or handling (NS) were administered to rats. Twenty-four hours after the last session, GH or GFP virus was infused bilaterally into the dorsal hippocampus. a) After three days of recovery, auditory trace conditioning was administered. Stress impaired trace conditioning, and this effect was reversed by intra-hippocampal GH. b) Long-term contextual fear memory was measured the next day by returning rats to the conditioning context for 5 m. Stress impaired contextual fear memory, and intra-hippocampal GH expression partially reversed this impairment. c) Long-term auditory fear memory was measured the following day by placing the rats in a novel context and presenting four tones in the absence of footshock. Stress impaired auditory fear memory, and intra-hippocampal GH expression fully reversed this effect. * indicates p<0.05 in a post-hoc comparison.

Results:

Stress did not affect the rapid acquisition of auditory trace fear conditioning (FIG. 3A; stress: $F(1,25)=0.02$, p=ns), and this was not differentially impacted by GH expression (Infusion X Stress interaction: $F(1,25)=0.17$, p=ns). In contrast, the effects of GH expression on long-term contextual and trace auditory fear memory did depend on stress (FIG. 3B; Infusion X Stress interaction: $F(1,25)=3.22$, p=0.08; and FIG. 3C; Infusion X Stress interaction: $F(1,25)=5.99$, p<0.05). Whereas rats in the STR-GFP group showed lower levels of conditional freezing than rats in the NS-GFP group, rats in the STR-GH group displayed levels of conditional freezing that were statistically indistinguishable from those displayed by rats in the NS-GFP group (FIG. 3B-C, post-hoc comparisons). These results show that the impairments in hippocampal function following chronic stress can be attributed to the loss of hippocampal GH.

Example 3: The Role of GH in Stress-Related Changes in Foreground Contextual Fear Conditioning To further investigate this, the role of GH in stress-related changes was also examined in foreground contextual fear conditioning, a hippocampus-dependent task (37). Rats were repeatedly exposed to daily immobilization stress (STR) or handling (NS). One day later, rats received intra-hippocampal infusions of either GH or GFP virus. After recovering for three days, rats were subjected to contextual fear conditioning. Long-term contextual memory was measured the next day.

Methods:
Subjects:
Rats were treated as described in Example 2.
Experimental Methods:
Growth hormone ELISA, Protein (Western) Immunoblot and Histology methods are as described in Example 2 Immobilization stress and Pavlovian Fear Conditioning were administered as described in the Methods of Example 2.

Figure 4:
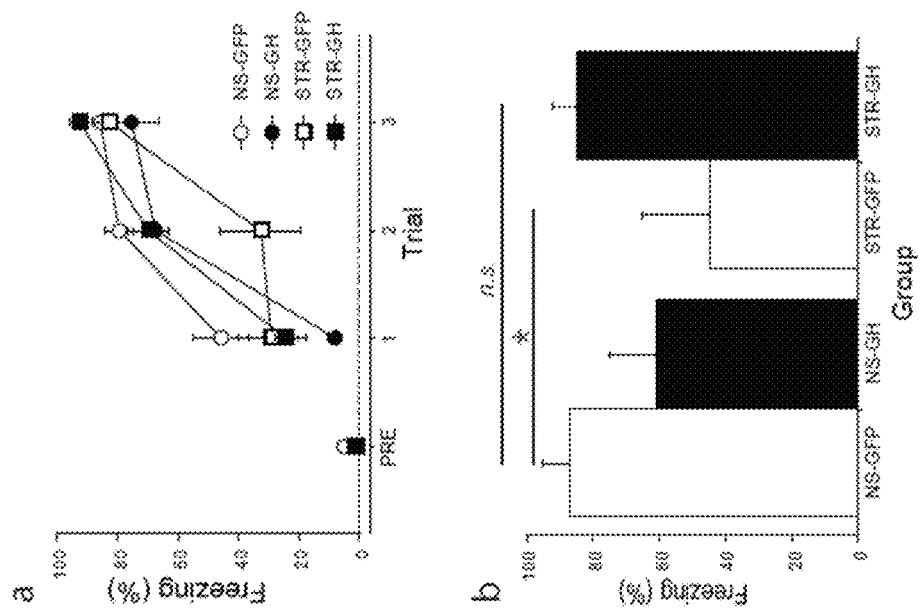
FIG. 4 shows that overexpression of hippocampal GH rescues stress-related impairments in contextual conditioning. Ten days of daily immobilization stress (STR) or handling (NS) were administered to rats. Twenty-four hours after the last session, GH or GFP virus was infused bilaterally into the dorsal hippocampus. a) After three days of recovery, contextual fear conditioning was administered. Stress slowed contextual fear acquisition, and this was prevented by intra-hippocampal GH. In contrast, intra-hippocampal GH had no effect in unstressed control rats. b) The next day, the rats were returned to the context for an 8 m context extinction session. Stress impaired long-term contextual fear memory, and this impairment was rescued by expression of GH in the dorsal hippocampus. In contrast, intra-hippocampal GH produced a mild impairment of long-term contextual fear memory in unstressed control rats. # indicates p<0.1 in a post-hoc comparison.

Results:

The effects of stress on contextual fear acquisition were dependent on the type of virus that had been infused in the hippocampus (FIG. 4A; Stress X Infusion interaction, $F(1,10)=1.35$, p<0.01): rats in the STR-GFP group displayed slower acquisition than rats in the STR-GH group (post-hoc comparisons). In contrast, rats in the NS-GFP and NS-GH groups acquired fear at virtually identical rates (post-hoc comparisons). Similar effects of GH were observed for long-term contextual memory (FIG. 4B; Stress X Infusion interaction, $F(1,10)=5.29$, p<0.05): intra-hippocampal GH rescued the memory-impairing effects of stress, leading to conditional freezing levels indistinguishable from NS-GFP controls (post-hoc comparisons). However, intra-hippocampal GH in unstressed controls produced a mild impairment in conditional freezing, relative to NS-GFP controls (p=0.09; post-hoc comparison). These results further confirm that a loss in hippocampal GH contributes to stress-related impairment in hippocampal function.

The examples provided herein demonstrate that chronic stress induces a profound and lasting downregulation of GH in the dorsal hippocampus. Animals that experienced chronic stress also exhibited significant impairment on two hippocampus-dependent tasks. When GH levels were increased in stressed animals using viral-mediated gene transfer, the animals did not exhibit any stress-related decrements in performance. This shows that a stress-induced loss of hippocampal GH contributes to stress-related impairment in hippocampal function, and that restoration of GH after stress termination is sufficient to reverse these changes.

Because GH can potentiate hippocampal synaptic plasticity, the overexpression of GH may lead to enhancement of hippocampal function. Interestingly, overexpression of GH in the hippocampus of unstressed animals had minimal effect on contextual or trace fear conditioning. For animals subjected to contextual fear conditioning, there was a mild trend for unstressed animals to have an impairment in long-term contextual fear memory when GH was overexpressed in hippocampus. This may be due to an occlusion effect, where GH may transiently saturate plasticity in the hippocampus such that synapses may not be further potentiated by learning. However, overexpression of GH clearly did not produce a broad occlusion of further hippocampus-dependent learning. The lack of occlusion may result from GH regulating its own expression, and viral expression of recombinant GH may have downregulated expression of endogenous GH. Regardless, these results support GH as a novel target for pharmacological intervention following stress in diseases, and show that interventions that boost GH signaling in hippocampus after stress may promote stress resilience.

Example 4: Amygdalar Growth Hormone is Increased by Chronic Stress

Growth hormone, a major effector of the ghrelin receptor, interacts with ghrelin in the amygdala to enhance fear memory. Although the pituitary expresses the highest levels of GH, it is also expressed in other brain regions, including the BLA.[44] It is not known how prolonged stress alters GH in the BLA. To test this, the impact of repeated immobilization stress (STR) or daily handling (NS) on GH levels in the BLA were examined. GH was readily detected in BLA homogenate and significantly upregulated 24 h after chronic stress (FIG. 5a, group: $F(1, 16)=6.44$, $P<0.05$), the time point at which increases are observed in circulating ghrelin and fear conditioning. This suggests that GH-mediated signaling in the BLA may be amplified following stress.

Figure 5:
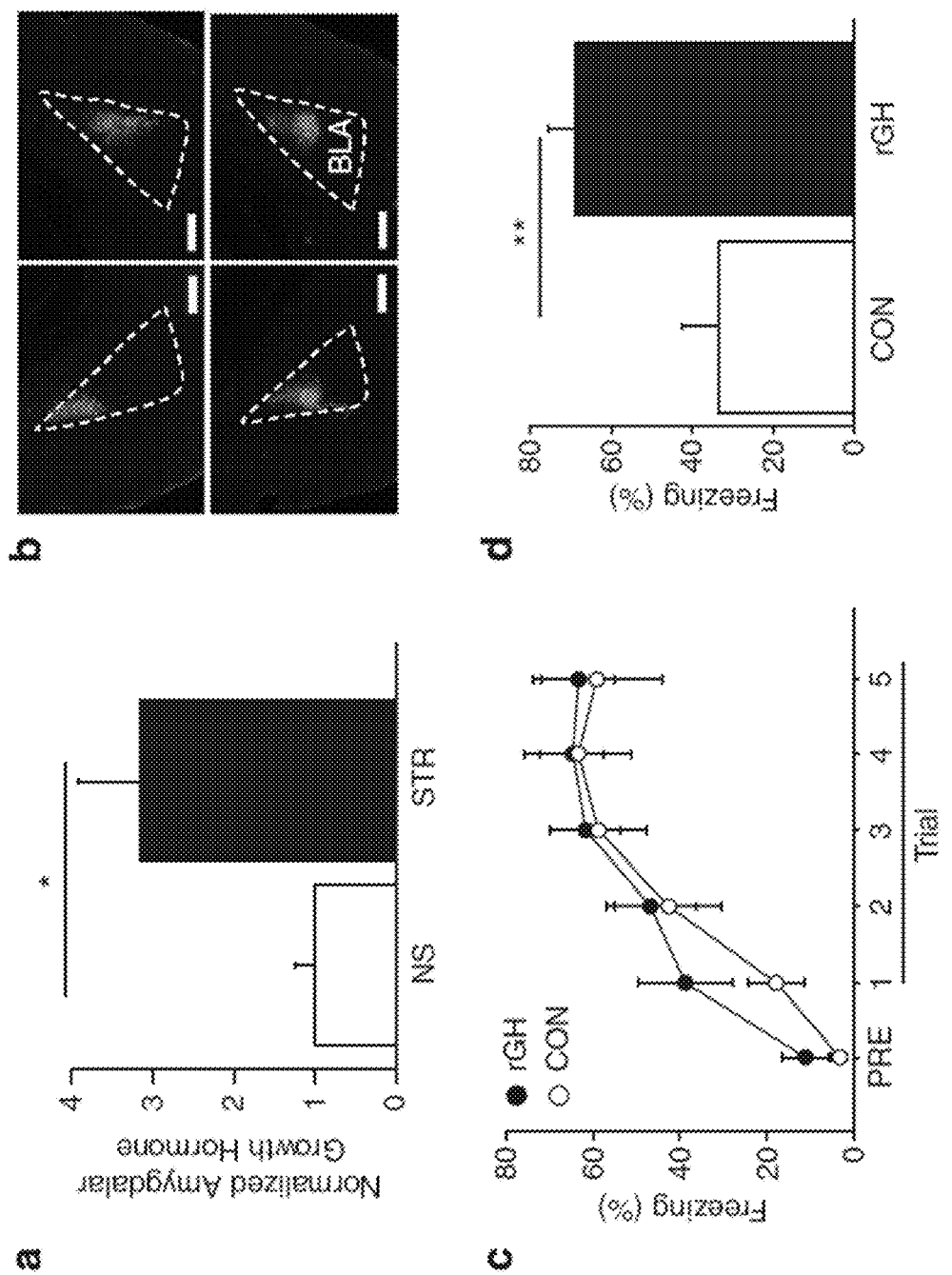
FIG. 5 shows that shows that amygdalar growth hormone is increased by chronic stress, is sufficient to enhance fear memory and is necessary for the fear potentiating effects of ghrelin receptor stimulation. a) Rats received either daily handling (no stress (NS)) or immobilization stress (STR) for 14 days. Animals were killed 24 h after the last stress or handling session and the basolateral complex of the amygdala (BLA) was dissected. Growth hormone (GH) levels in the BLA were measured using enzyme-linked immunosorbent assay (ELISA). b) The herpes simplex virus (HSV)-based viral vectors expressing either green fluorescent protein (GFP; CON) or recombinant rat GH (rGH) was infused in the BLA and expression was assessed after behavioral testing was complete. Representative GFP expression from two rats is shown. c) Auditory Pavlovian fear conditioning was performed 3 days after HSV virus infusions. d) Long-term fear memory was assessed by placing the animals in a novel context and measuring conditional freezing following tone presentation 48 h after the conditioning session. e) Short-term BLA cell cultures were used to measure GH release following treatment with a ghrelin receptor agonist (MK) or vehicle (VEH). f) Adeno-associated virus (AAV) constructs were generated to examine the contribution of GH-mediated signaling in the BLA to ghrelin-induced potentiation of fear. g) Following infusion of the AAVs into the BLA and recovery, rats received 10 days of systemic injection of either a ghrelin receptor agonist (MK) or vehicle (VEH). After 24 h, auditory Pavlovian fear conditioning was administered to all rats. h) Long-term fear memory was assessed by placing the animals in a novel context and measuring conditional freezing following tone presentation 48 h after the conditioning session. Scale bar, is 500 mm. All data are mean±s.e.m. *P<0.05, **P<0.01 in planned comparisons.
Figure 5:
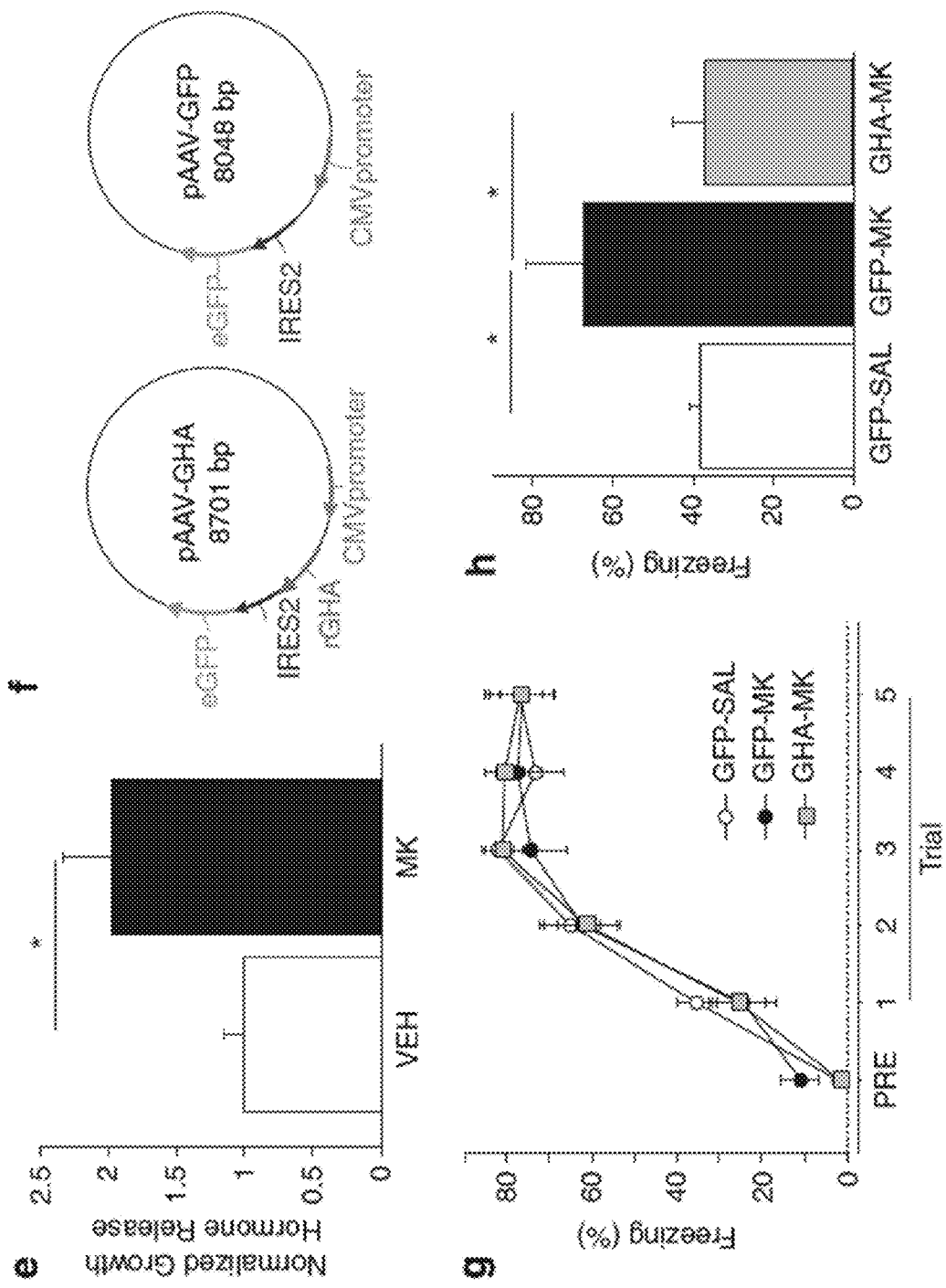

GH can induce synaptic plasticity[46] and is increased in response to learning,[47] but it is unclear how it affects amygdala function. Herpes simplex-based viral vectors were used to express recombinant rat GH and a GFP reporter or GFP only.[51] Naive rats received intra-BLA infusions of either the recombinant rat GH virus or the GFP-only control virus (CON) (FIG. 5b). After 3 days, when herpes simplex virus-mediated transgene expression is at its maximum,[48] auditory fear conditioning was administered. Fear to the tone was assessed 48 h later. Overexpression of recombinant rat GH did not alter fear acquisition (FIG. 5c; infusion×trial interaction: $F(4, 52)=0.57$, P=ns) but did enhance long-term fear memory (FIG. 5d, infusion: $F(1, 13)=9.97$, $P<0.01$). These data demonstrate that high levels of GH in the BLA are sufficient to enhance fear learning, an effect that is similar to the effect of repeated intra-BLA ghrelin receptor stimulation.

To determine whether ghrelin receptor stimulation in amygdala triggers the release of GH as it does from the pituitary,[43] short-term cultures were generated of BLA cells and measured GH protein in the media following treatment with either MK-0677 or vehicle. Stimulation of the ghrelin receptor in BLA cells led to significantly elevated release of GH (FIG. 5e; treatment: $F(1, 8)=8.24$, $P<0.05$). These results show that ghrelin receptor stimulation can trigger GH release from the amygdala.

Because ghrelin and GH can interact in amygdala, we next determined whether GH is a necessary downstream signaling partner for the fear-enhancing effects of repeated ghrelin receptor stimulation. An AAV viral construct to overexpress a mutant form of the rat GH protein (GHA) that acts as a functional antagonist to endogenous GH was generated.[49,50] Following infusion of AAV to overexpress either GHA or a control protein (GFP) (FIG. 5f), rats were permitted to recover for 5 weeks. After recovery, rats that were infused with GHA received daily injections of either the ghrelin receptor agonist MK-0677 (MK) or saline (SAL) for 10 days. Rats that were infused with GFP received daily injections of SAL for 10 days. At 24 h after the final injection, all rats were subjected to auditory fear conditioning, followed by assessment of long-term auditory fear memory in a subsequent session 48 h later. Although no differences were observed between any group during fear conditioning (FIG. 5g; group: $F(2, 13)=0.07$; P=ns), differences in long-term fear memory were observed (FIG. 5h; group: $F(2, 13)=4.32$, $P<0.05$). Specifically, antagonizing the activity of GH prevented the fear-enhancing effects of repeated ghrelin receptor agonism (FIG. 5h; planned comparisons between GFP-SAL vs GFP-MK and GFP-MK vs GHA-MK). These data reveal that repeated ghrelin receptor stimulation requires GH-dependent signaling in the amygdala to exert its fear-enhancing effects.

REFERENCES

1. B. McEwen and J. C. Wingfield: Allostasis and allostatic load. In: *Encyclopedia of Stress*. Ed G. Fink. Academic Press, New York (2007)
2. R. P. Juster, G. Bizik, M. Picard, G. Arsenault-Lapierre, S. Sindi, L. Trepanier, M. F. Marin, N. Wan, Z. Sekerovic, C. Lord, A. J. Fiocco, P. Plusquellec, B. S. McEwen and S. J. Lupien: A transdisciplinary perspective of chronic stress in relation to psychopathology throughout life span development. *Dev Psychopathol*, 23(3), 725-76 (2011) doi:S0954579411000289 [pii] 10.1017/S0954579411000289
3. B. S. McEwen: Protective and damaging effects of stress mediators. *N Engl J Med*, 338(3), 171-9 (1998) doi:10.1056/NEJM199801153380307
4. C. Mazure: Does Stress Cause Psychiatric Illness? American Psychiatric Press, Inc., Washington, D.C. (1995)
5. F. Lederbogen, P. Kirsch, L. Haddad, F. Streit, H. Tost, P. Schuch, S. Wust, J. C. Pruessner, M. Rietschel, M. Deuschle and A. Meyer-Lindenberg: City living and urban upbringing affect neural social stress processing in humans. *Nature*, 474(7352), 498-501 (2011) doi:nature10190 [pii] 10.1038/nature10190
6. J. K. Belanoff, M. Kalehzan, B. Sund, S. K. Fleming Ficek and A. F. Schatzberg: Cortisol activity and cognitive changes in psychotic major depression. *Am J Psychiatry*, 158(10), 1612-6 (2001)
7. A. Jeneson and L. R. Squire: Working memory, long-term memory, and medial temporal lobe function. *Learn Mem*, 19(1), 15-25 (2012) doi:19/1/15 [pii] 10.1101/1m.024018.111
8. D. A. Bangasser and T. J. Shors: The hippocampus is necessary for enhancements and impairments of learning following stress. *Nat Neurosci*, 10(11), 1401-3 (2007)
9. K. A. Goosens: Hippocampal regulation of aversive memories. *Curr Opin Neurobiol*, 21(3), 460-6 (2011) doi:50959-4388(11)00048-1 [pii] 10.1016/j.conb.2011.04.003
10. T. J. Shors, C. Chua and J. Falduto: Sex differences and opposite effects of stress on dendritic spine density in the male versus female hippocampus. *J Neurosci*, 21(16), 6292-7 (2001)
11. Y. Chen, C. M. Dube, C. J. Rice and T. Z. Baram: Rapid loss of dendritic spines after stress involves derangement of spine dynamics by corticotropin-releasing hormone. *J Neurosci*, 28(11), 2903-11 (2008) doi:28/11/2903 [pii] 10.1523/JNEUROSCI.0225-08.2008
12. T. J. Shors: Acute stress rapidly and persistently enhances memory formation in the male rat. *Neurobiol Learn Mem*, 75(1), 10-29 (2001) doi:10.1006/nlme 1999.395651074-7427(99)93956-4
13. D. J. de Quervain, B. Roozendaal and J. L. McGaugh: Stress and glucocorticoids impair retrieval of long-term spatial memory. *Nature*, 394(6695), 787-90 (1998) doi:10.1038/29542
14. D. M. Diamond, A. M. Campbell, C. R. Park, J. Halonen and P. R. Zoladz: The temporal dynamics model of emotional memory processing: a synthesis on the neurobiological basis of stress-induced amnesia, flashbulb and traumatic memories, and the Yerkes-Dodson law. *Neural Plast*, 60803 (2007)
15. A. M. Magarinos and B. S. McEwen: Stress-induced atrophy of apical dendrites of hippocampal CA3c neurons: involvement of glucocorticoid secretion and excitatory amino acid receptors. *Neuroscience*, 69(1), 89-98 (1995)
16. Y. Watanabe, E. Gould and B. S. McEwen: Stress induces atrophy of apical dendrites of hippocampal CA3 pyramidal neurons. *Brain Res*, 588(2), 341-5 (1992)
17. C. Sandi, H. A. Davies, M. I. Cordero, J. J. Rodriguez, V. I. Popov and M. G. Stewart: Rapid reversal of stress 17. induced loss of synapses in CA3 of rat hippocampus following water maze training. *Eur J Neurosci*, 17(11), 2447-56 (2003)
18. A. Vyas, R. Mitra, B. S. Shankaranarayana Rao and S. Chattarji: Chronic stress induces contrasting patterns of dendritic remodeling in hippocampal and amygdaloid neurons. *J Neurosci*, 22(15), 6810-8 (2002)
19. R. Pawlak, B. S. Rao, J. P. Melchor, S. Chattarji, B. McEwen and S. Strickland: Tissue plasminogen activator and plasminogen mediate stress-induced decline of neuronal and cognitive functions in the mouse hippocampus. *Proc Natl Acad Sci USA*, 102(50), 18201-6 (2005)
20. J. Nishimura, Y. Endo and F. Kimura: A long-term stress exposure impairs maze learning performance in rats. *Neurosci Lett*, 273(2), 125-8 (1999)
21. J. K. Kleen, M. T. Sitomer, P. R. Killeen and C. D. Conrad: Chronic stress impairs spatial memory and motivation for reward without disrupting motor ability and motivation to explore. *Behav Neurosci*, 120(4), 842-51 (2006)
22. H. Lakshminarasimhan and S. Chattarji: Stress leads to contrasting effects on the levels of brain derived neurotrophic factor in the hippocampus and amygdala. *PLoS One*, 7(1), e30481 (2012) doi:10.1371/journal.pone.0030481PONE-D-11-18672 [pii]
23. F. Nyberg and P. Burman: Growth hormone and its receptors in the central nervous system—location and functional significance. *Horm Res*, 45(1-2), 18-22 (1996)
24. L. Y. Sun, K. Al-Regaiey, M. M. Masternak, J. Wang and A. Bartke: Local expression of GH and IGF-1 in the hippocampus of GH-deficient long-lived mice. *Neurobiol Aging*, 26(6), 929-37 (2005)doi: S01974580(04)002842 [pii] 10.1016/j.neurobiolaging.2004.07.010
25. N. R. Zearfoss, J. M. Alarcon, P. Trifilieff, E. Kandel and J. D. Richter: A molecular circuit composed of CPEB-1 and c-Jun controls growth hormone-mediated synaptic plasticity in the mouse hippocampus. *J Neurosci*, 28(34), 8502-9 (2008) doi:28/34/8502 [pii] 10.1523/JNEUROSCI. 1756-08.2008
26. G. S. Mahmoud and L. M. Grover: Growth hormone enhances excitatory synaptic transmission in area CA1 of rat hippocampus. *J Neurophysiol*, 95(5), 2962-74 (2006) doi:00947.2005 [pii] 10.1152/jn.00947.2005
27. D. P. Molina, 0. J. Ariwodola, C. Linville, W. E. Sonntag, J. L. Weiner, J. K. Brunso-Bechtold and M. M. Adams: Growth hormone modulates hippocampal excitatory synaptic transmission and plasticity in old rats. *Neurobiol Aging*, 33(9), 1938-49 (2012) doi:S0197-4580(11)00351-4 [pii] 10.1016/j.neurobiolaging.2011.09.014
28. C. P. Donahue, R. V. Jensen, T. Ochiishi, I. Eisenstein, M. Zhao, T. Shors and K. S. Kosik: Transcriptional profiling reveals regulated genes in the hippocampus during memory formation. *Hippocampus*, 12(6), 821-33 (2002)
29. M. N. Treacy, F. Ryan and F. Martin: Functional glucocorticoid inducible enhancer activity in the 5'-flanking sequences of the rat growth hormone gene. *J Steroid Biochem Mol Biol*, 38(1), 1-15 (1991) doi:0960-0760(91)90395-L [pii]
30. C. P. Donahue, K. S. Kosik and T. J. Shors: Growth hormone is produced within the hippocampus where it responds to age, sex, and stress. *Proc Natl Acad Sci USA*, 103(15), 6031-6 (2006)
31. P. H. Seeburg, J. Shine, J. A. Martial, J. D. Baxter and H. M. Goodman: Nucleotide sequence and amplification in bacteria of structural gene for rat growth hormone. *Nature*, 270(5637), 486-94 (1977)
32. D. Kaufer, W. O. Ogle, Z. S. Pincus, K. L. Clark, A. C. Nicholas, K. M. Dinkel, T. C. Dumas, D. Ferguson, A. L. Lee, M. A. Winters and R. M. Sapolsky: Restructuring the neuronal stress response with anti-glucocorticoid gene delivery. *Nat Neurosci*, 7(9), 947-53 (2004)
33. P. Lim and R. Neve: Generation of High-Titer Defective HSV-1 Vectors. In: *Current Protocols in Neuroscience*. John Wiley and Sons, Inc., (2000)
34. G. Paxinos and C. Watson: The Rat Brain in Stereotaxic Coordinates—The New Coronal Set, Fifth Edition. Elsevier Academic Press, San Diego (2005)
35. T. J. Shors, C. Weiss and R. F. Thompson: Stress-induced facilitation of classical conditioning. *Science*, 257(5069), 537-9 (1992)
36. J. D. Raybuck and K. M. Lattal: Double dissociation of amygdala and hippocampal contributions to trace and delay fear conditioning. *PLoS One*, 6(1), e15982 doi: 10.1371/journal.pone.0015982
37. S. G. Anagnostaras, G. D. Gale and M. S. Fanselow: Hippocampus and contextual fear conditioning: recent controversies and advances. *Hippocampus*, 11(1), 8-17 (2001) doi: 10.1002/1098-1063 (2001)11:1<8::AID-HIPO1015>3.0.CO; 2-7
38. M. Le Greves, P. Steensland, P. Le Greves and F. Nyberg: Growth hormone induces age-dependent alteration in the expression of hippocampal growth hormone receptor and N-methyl-D-aspartate receptor subunits gene transcripts in male rats. *Proc Natl Acad Sci USA*, 99(10), 7119-23 (2002) doi:10.1073/pnas.09213539999/10/7119 [pii]
39. Y. P. Tang, E. Shimizu, G. R. Dube, C. Rampon, G. A. Kerchner, M. Zhuo, G. Liu and J. Z. Tsien: Genetic enhancement of learning and memory in mice. *Nature*, 401(6748), 63-9 (1999) doi:10.1038/43432
40. M. I. Ransome and A. M. Turnley: Growth hormone signaling and hippocampal neurogenesis: insights from genetic models. *Hippocampus*, 18(10), 1034-50 (2008) doi:10.1002/hipo.20463
41. B. Vollmayr, C. Simonis, S. Weber, P. Gass and F. Henn: Reduced cell proliferation in the dentate gyrus is not correlated with the development of learned helplessness. *Biol Psychiatry*, 54(10), 1035-40 (2003) doi: S0006322303005274 [pii]
42. M. Fleshner, S. F. Maier, D. M. Lyons and M. A. Raskind: The neurobiology of the stress-resistant brain. *Stress*, 14(5), 498-502 (2011) doi:10.3109/10253890.2011.596865
43. Kojima M, Hosoda H, Date Y, Nakazato M, Matsuo H, Kangawa K. Ghrelin is a growth-hormone-releasing acylated peptide from stomach. Nature 1999; 402:656-660.
44. Donahue C P, Kosik K S, Shors T J. Growth hormone is produced within the hippocampus where it responds to age, sex, and stress. Proc Natl Acad Sci USA 2006; 103: 6031-6036.
45. Pacold S T, Kirsteins L, Hojvat S, Lawrence A M. Biologically active pituitary hormones in the rat brain amygdaloid nucleus. Science 1978; 199: 804-806.
46. Mahmoud G S, Grover L M. Growth hormone enhances excitatory synaptic transmission in area CA1 of rat hippocampus. J Neurophysiol 2006; 95: 2962-2974.
47. Donahue C P, Jensen R V, Ochiishi T, Eisenstein I, Zhao M, Shors T et al. Transcriptional profiling reveals regulated genes in the hippocampus during memory formation. Hippocampus 2002; 12: 821-833.
48. Carlezon Jr. W A, Thome J, Olson V G, Lane-Ladd S B, Brodkin E S, Hiroi N et al. Regulation of cocaine reward by CREB. Science 1998; 282: 2272-2275.

49. Chen W Y, Wight D C, Mehta B V, Wagner T E, Kopchick J J. Glycine 119 of bovine growth hormone is critical for growth-promoting activity. Mol Endocrinol 1991; 5: 1845-1852.
50. Chen W Y, Wight D C, Wagner T E, Kopchick J J. Expression of a mutated bovine growth hormone gene suppresses growth of transgenic mice. Proc Natl Acad Sci USA 1990; 87: 5061-5065.
51. Vander Weele C M, Saenz C, Yao J, Correia S S, Goosens K A. Restoration of hippocampal growth hormone reverses stress-induced hippocampal impairment. Front Behav Neurosci 2013; 7: 66.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for treating a stress sensitive condition, comprising administering to a subject having or at risk of having a stress sensitive condition a growth hormone (GH) antagonist in an effective amount to treat the stress sensitive condition, wherein the stress sensitive condition is a stress sensitive disorder selected from post-traumatic stress disorder (PTSD), acute stress disorder, generalized anxiety disorder, obsessive-compulsive disorder, panic disorders, or trichotillomania.

2. The method of claim 1, wherein the GH antagonist is a growth hormone receptor (GHR) antagonist.

3. The method of claim 1, wherein the GHR antagonist is a protein growth hormone receptor antagonist and is pegvisomant (SOMAVERT®), B2036, B2036-PEG, G120R, G120RhGH, or analogs thereof.

4. The method of claim 1, wherein the stress sensitive disorder is PTSD.

5. The method of claim 1 wherein subject has been associated with military service or a natural disaster.

6. The method of claim 1, wherein the GH antagonist is administered systemically.

7. The method of claim 1, wherein the GH antagonist is administered while the subject is experiencing the stress.

8. The method of claim 1, wherein the GH antagonist is administered only during the time that the subject is experiencing the stress.

9. The method of claim 1, wherein the GH antagonist is administered to the subject in a sustained release device.

10. The method of claim 1, wherein the GH antagonist is administered to the subject orally.

11. The method of claim 1, wherein the GH antagonist is administered to the subject intravenously.

12. The method of claim 1, wherein the GH antagonist is administered before, during and/or after exposure of the subject to chronic stress.

13. The method of claim 1, wherein the GH antagonist is delivered to the amygdala.

14. A method for treating a stress sensitive condition, comprising administering to a subject an effective amount of a growth hormone (GH) antagonist, wherein the stress sensitive condition is bipolar disorder.

* * * * *